United States Patent [19]

Dove et al.

[11] Patent Number: 5,179,579
[45] Date of Patent: Jan. 12, 1993

[54] RADIOGRAPH DISPLAY SYSTEM WITH ANATOMICAL ICON FOR SELECTING DIGITIZED STORED IMAGES

[75] Inventors: S. Brent Dove; W. Doss McDavid, both of San Antonio, Tex.; C. Donald Wilcox, O'Fallon, Ill.

[73] Assignee: Board of Regents, The University of Texas System, Austin, Tex.

[21] Appl. No.: 717,211

[22] Filed: Jun. 17, 1991

[51] Int. Cl.$^5$ .............................................. A61B 6/14
[52] U.S. Cl. ........................................ 378/38; 378/39; 378/40; 378/99; 378/162; 378/165; 378/901; 378/170; 378/168; 378/205; 364/413.13; 364/413.15; 364/413.22
[58] Field of Search ................... 378/99, 38, 165, 162, 378/901, 40, 39, 62, 170, 168, 205; 364/413.22, 413.13, 413.15, 413.16

[56] References Cited

U.S. PATENT DOCUMENTS

| | | | |
|---|---|---|---|
| 4,409,616 | 10/1983 | Ledley | 378/40 |
| 4,837,732 | 6/1989 | Brandestini et al. | 364/413.28 |
| 4,852,134 | 7/1989 | Kinanen et al. | 378/38 |
| 4,856,038 | 8/1989 | Guenther et al. | 378/39 |
| 4,878,234 | 10/1989 | Pfeiffer et al. | 378/40 |
| 5,018,177 | 5/1991 | McDavid et al. | 378/62 |
| 5,021,770 | 6/1991 | Alsaka et al. | 378/99 |

OTHER PUBLICATIONS

Trophy Mini-Julie User's Manual, Jan. 1991.

Langland, et al., *Textbook of Dental Radiology*, Charles C. Thomas, Publisher, pp. 308-314.

Primary Examiner—Janice A. Howell
Assistant Examiner—Kim-Kwok Chu
Attorney, Agent, or Firm—Arnold, White & Durkee

[57] ABSTRACT

A method and apparatus for storing and displaying radiographs, particularly intra-oral radiographs, is presented. Radiographs are captured, digitized, and displayed along with an icon of a portion of the anatomy from which the radiograph was taken. The anatomical sites represented by the icon are arranged according to their normal anatomical relationship. The icon is used by the system user to select a portion of the anatomy corresponding to the displayed radiograph, and the radiograph is stored along with indicia of the selected anatomical site. Then, when the stored radiograph is desired to be viewed, the icon is again displayed, and the appropriate anatomical site is selected, which causes the corresponding radiograph to be retrieved from storage and displayed. When processing intra-oral radiographs, the icon can take the form of a dental film holder, with the positions of the film holder corresponding to anatomical sites readily recognized by dentists, each position of the film holder being arranged in anatomical relation to other positions of the film holder icon. An image of dentition, for example, a dental arch, can also be used as an icon to facilitate the storage and display of intra-oral radiographs.

5 Claims, 5 Drawing Sheets

Fig. 2

| MODALITY | EXAM. TYPE | DATE OF EXAM |
|---|---|---|
| PANORAMIC | COMPLETE | 5/12/90 |
| INTRAORAL | FMX-20 | 5/12/90 |
| INTRAORAL | BW-4 | 8/12/89 |
| INTRAORAL | BW-2 | 1/25/89 |
| EXTRAORAL | CEPHALOMETRIC | 4/4/88 |

Pt. NAME ___ 38
CHART # ___ 39      MODALITY ___ 47
DOB ___ 41            EXAM TYPE ___ 48
DOE ___ 42            INTERPRETATION ___ 49
TOE ___ 43
REFERING
DOCTOR ___ 44      MANUAL  CINE
SERVICE ___ 46          51      52

Fig. 3

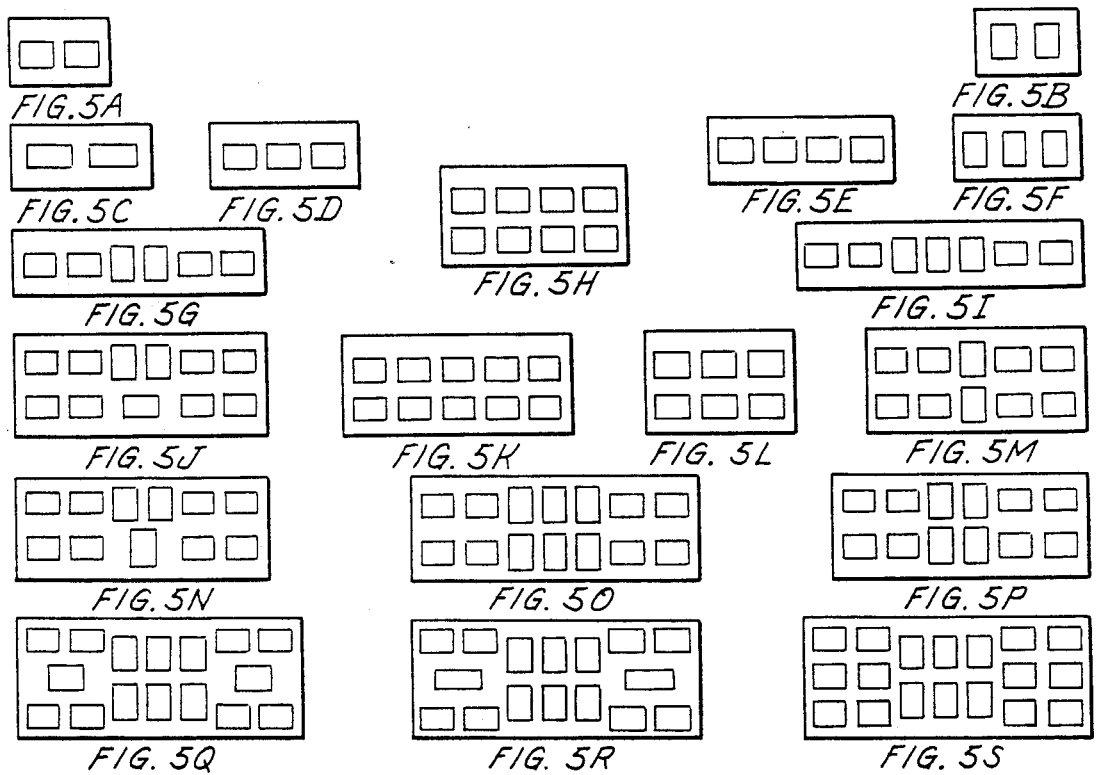
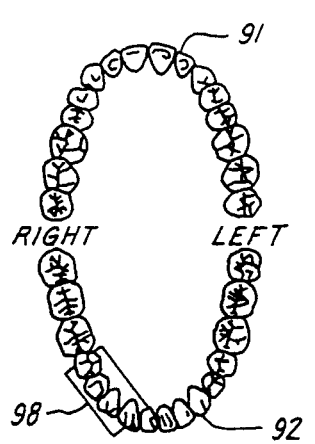
*Fig. 6*
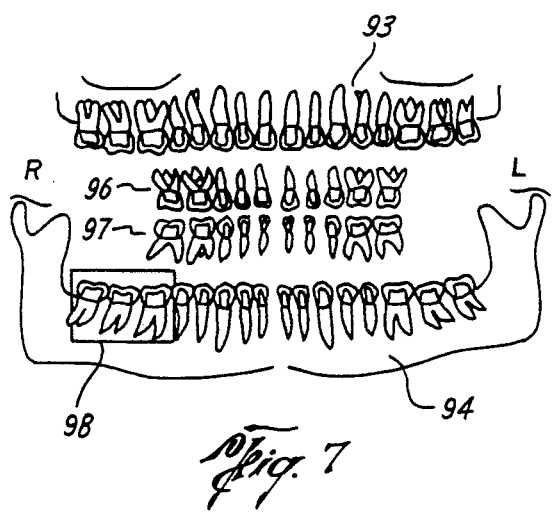
*Fig. 7*

RADIOGRAPH DISPLAY SYSTEM WITH ANATOMICAL ICON FOR SELECTING DIGITIZED STORED IMAGES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF INVENTION

The invention relates to methods and apparatus for displaying stored radiographs, particularly intra-oral radiographs.

It is well known in the field of oral radiology to mount dental radiographs in a film holder. Use of such film holders minimizes the possibility of misinterpretation of radiographs which, when loose and unmounted, can appear to be quite similar to one another. Such film holders can hold as few as one dental radiograph, or as many as 20 or more radiographs. Interpretation of such mounted radiographs is facilitated by mounting each film in normal anatomic relation to each other. In other words, each mounting position in a dental film holder corresponds to a particular anatomical site or anatomical region. Such mounting of dental radiographs also facilitates repeated study and comparison of sets of radiographs taken at different times in order, for example, to assess the progress of a particular dental treatment.

In addition, the mounting of dental radiographs in film holders in normal anatomic relation allows a dentist, having knowledge of normal radiologic anatomy and knowledge of anatomical landmarks, to quickly and easily interpret any set of mounted dental radiographs. The anatomical landmarks used by dentists include: the maxillary molar area (including the posterior wall of the maxillary tuberosity, the hamular process, the coronoid process of the mandible, the maxillary sinus, and the zygomatic process); the maxillary premolar area (including the maxillary sinus); the maxillary incisor area (including the incisive foramen, the cartilage of the nose, the nasal septum, and the nasal fossae); the mandibular molar area (including the external oblique line, the mylohyoid ridge and the mandibular canal); the mandibular premolar area (including the mylohyoid ridge and the mental foramen); and the mandibular incisor area (including the mental ridges, lingual foramen and the genial tubercles). Film holders present films taken of these anatomical landmark sites in positions that are consistent from holder to holder.

Recent advances in dental radiology include the use of x-ray sensitive sensors in place of film to produce digitized x-ray images which are stored in a computer memory and viewed on a computer monitor. In one such computer system, intra-oral x-ray images are created and stored along with information regarding patient identification and the number of the tooth in the image. Sets of images (constituting, for example, a dental survey), can be stored and recalled for display. When sets of related images are displayed, miniature versions of the images are presented in one portion of the display monitor for selection by the user, and are displayed in another portion of the monitor.

However, these miniature representations of the images are in no particular order, requiring the user carefully to assess which image among the set of images is the image desired to be displayed and studied. This system becomes particularly awkward as the number of images in a set increases given the fact intra-oral radiographs of different anatomical sites can appear to be quite similar.

SUMMARY OF THE INVENTION

The present invention solves the above-noted drawbacks of the prior art by providing a method and apparatus for displaying stored radiographic images which takes advantage of dentists' knowledge of normal radiologic anatomy and knowledge of anatomical landmarks.

In particular, the present invention includes an x-ray sensor and x-ray source which are used together to produce images of target anatomical sites. The images are then stored, preferably after digitization, in a computer memory. Then, the display of the stored images is facilitated by use of a representation or icon of anatomical sites, or of the portion of the anatomy, from which the images were taken. The system user selects the image to be displayed by selecting the appropriate anatomical site from the representation of anatomical sites or portion of anatomy.

The preferred application for the present invention is in intra-oral radiology. In such an application, sets of stored radiographs are displayed by using a representation of a dental film holder, or of dentition such as a dental arch. The system user selects the portion of the representation corresponding to the desired image to be displayed, and the desired image is then retrieved and displayed. Use of a representation of a dental film holder permits a dentist to use his or her knowledge of the anatomical significance of the positions of the mounting positions in the film holder.

Thus, the present invention combines the organizational and interpretational advantages of film holders, with the advantages of digital x-ray imaging techniques.

REFERENCE TO APPENDIX

A source code listing of a computer program that embodies the present invention is included in an Appendix to this patent document.

BRIEF DESCRIPTION OF THE DRAWINGS

FIG. 2 is a screen display, in accordance with the present invention, produced by the apparatus of FIG. 1.

FIG. 3 is another screen display, in accordance with the present invention, produced by the apparatus of FIG. 1.

FIGS. 5A-S are examples of representations of film holders usable a icons in the present invention.

FIGS. 6 and 7 are examples of representations of dentition, usable a icons in the present invention.

DETAILED DESCRIPTION OF THE PREFERRED EMBODIMENTS

Figure 1:
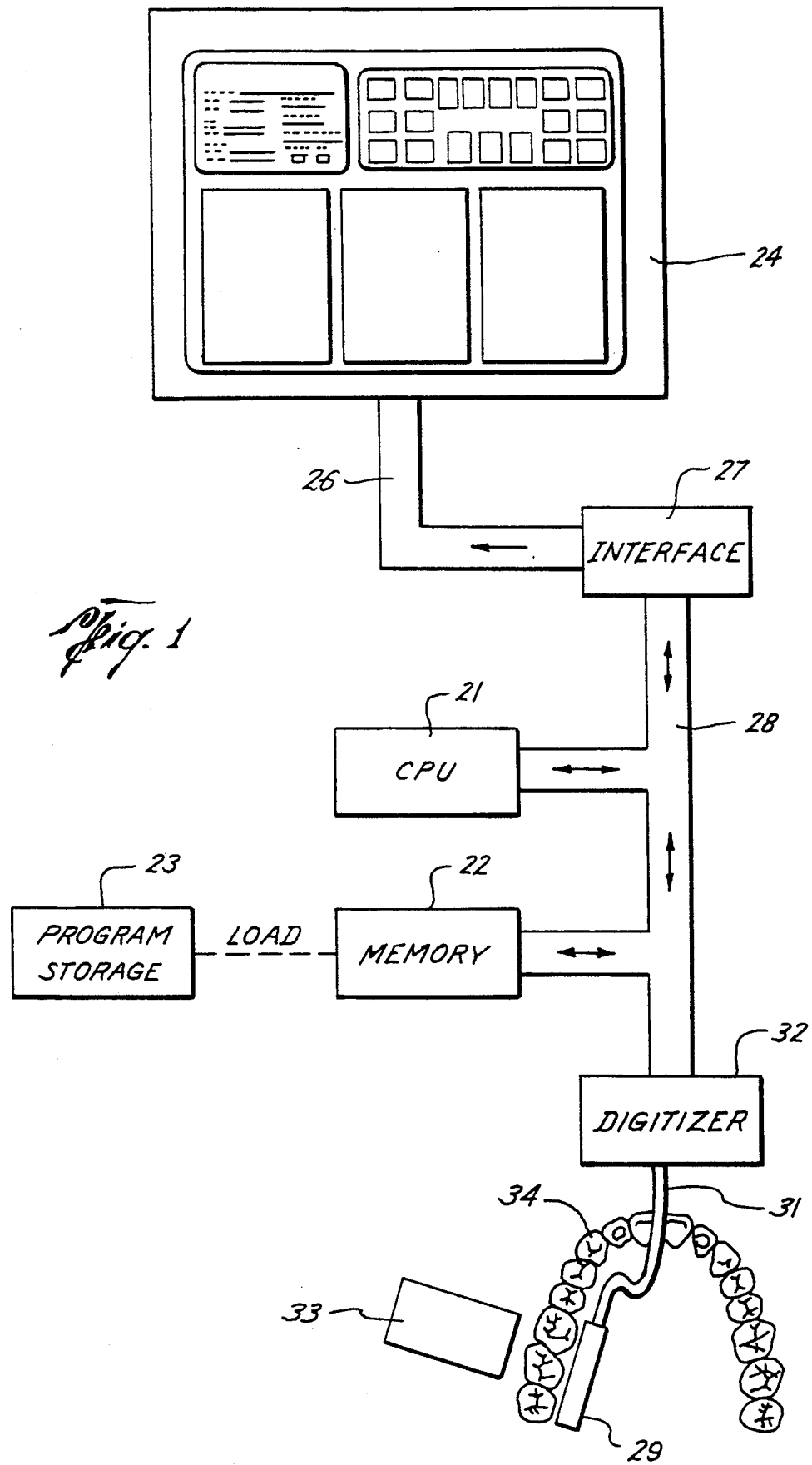
FIG. 1 is an apparatus embodying the present invention.

Referring to FIG. 1, a computer-based system is presented embodying the present invention.

The computer-based system includes central processing unit (CPU) 21, which, in operation, first loads software embodying the present invention into memory 22 from program storage medium 23. The software of the present invention is presented in flow chart form in FIGS. 4A and 4B, and is shown in detail in the program listing of the Appendix hereto. Program storage medium 23 can be any machine readable storage medium such as, for example, a floppy or hard magnetic or optical disk, or a programmable read-only memory. The computer system further includes display 24 which is connected in a known manner through display control bus 26, display interface 27, and internal data/address bus 28 to CPU 21. The computer-based system also includes an x-ray sensor 29 which is connected through sensor cable 31, digitizer 32, and internal data/address bus 28 to CPU 21. To acquire x-ray images, sensor 29 is used with x-ray source 33 to produce two-dimensional x-ray images of dentition 34.

The computer system can be any computer and hardware display. In the preferred embodiment, an IBM AT compatible PC computer, available from Jameco Electronics is used. This preferred computer system includes an Intel 33 MHz 80386 CPU with 8 megabytes of system RAM, 40 megabytes of hard disk drive, 5.25 and 3.5 inch floppy disk drives, a SuperVGA noninterlaced 1024×768 pixel display adapter, a noninterlaced SuperVGA monitor, and an AT 101 key style keyboard. However, other combinations of commercially available components can also be used without departing from the scope of the invention.

The preferred x-ray sensor is a Sens-A-Ray sensor, available from Regam Medical Systems AB. This preferred sensor produces a 576×386 pixel analog image which is digitized by digitizer 32 before application to data/address bus 28. Digitizer 32 is preferably a framegrab board available from Regam Medical Systems AB, however, other commercially available image digitizers can also be used. Digitizer 32 is required in the preferred embodiment because the preferred sensor 29 produces a pixelized analog signal. However, if sensor 29 produced a digital signal, sensor 29 could be connected directly to data/address bus 28, and digitizer 32 could be eliminated.

X-ray source 33 can be any commercially available x-ray source appropriate for the particular application. For example, for intra-oral radiography, x-ray source 33 can be, for example, a type Gendex 1000 x-ray source available from Gendex Corp. Of course, other types of commercially available x-ray sources are also acceptable.

Figure 3:
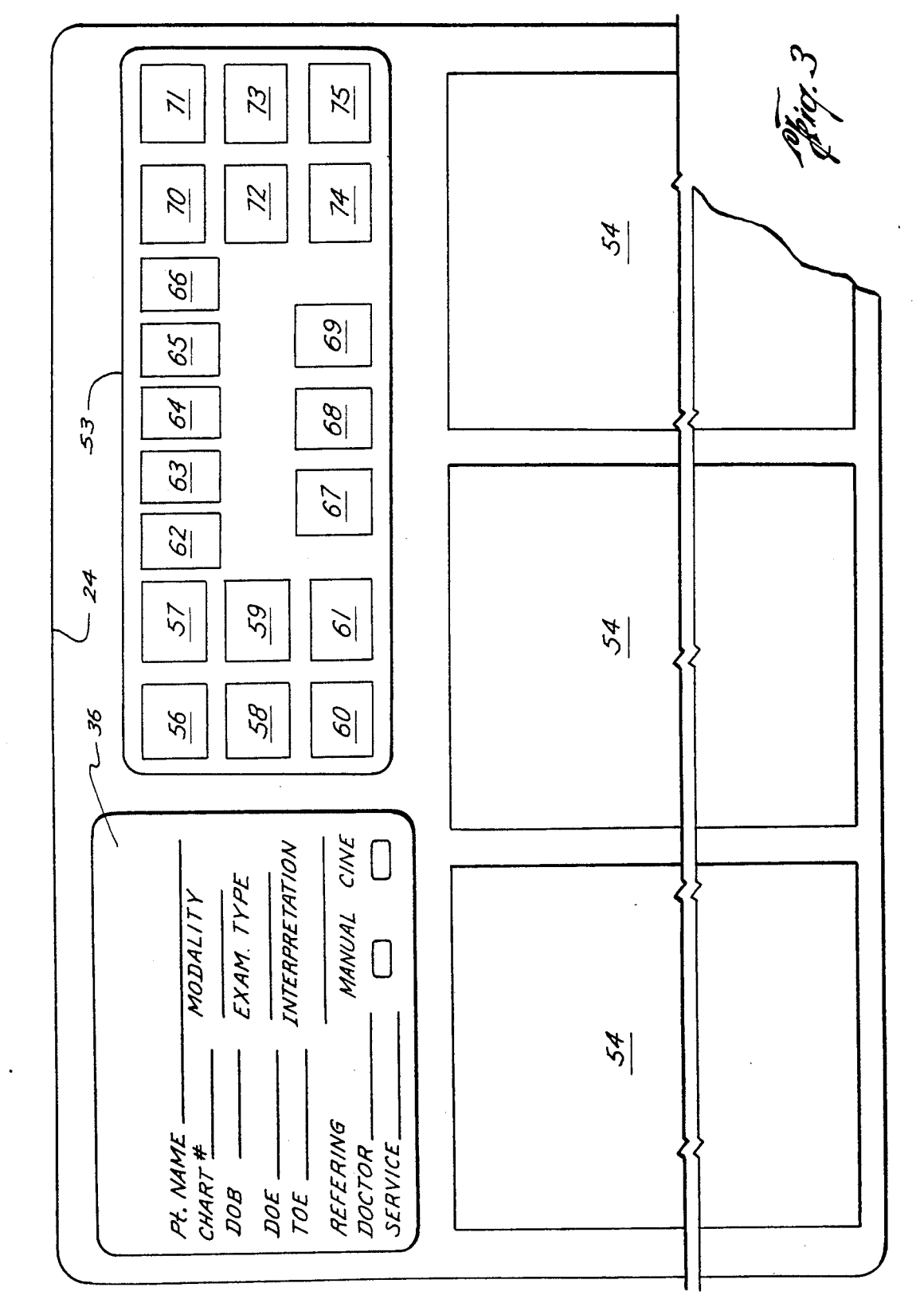

Referring now to FIGS. 2 and 3, shown are images displayed on display 24 (FIG. 1) which are illustrative of the present invention. Referring first to FIG. 2, shown is a patient query dialog field 36 and exam/study selection dialog field 37. Patient query dialog field 36 includes several subfields in which are entered patient specific data. For example, subfields 38, 39 and 41 include, respectively, the patient's name, the patient's chart number, and the patient's date of birth. Subfields 42 and 43 respectively display the date and time of examination. Subfields 44 and 46 relate to the referring physician.

Subfield 47 displays the modality of the particular examination (for example panoramic, intra-oral, extraoral), and subfield 48 displays the type of examination (for example full mouth, bitewing, complete panorama, cephalometric). Subfield 49 reveals the interpretation status, and subfields 51 and 52 indicate whether the user wishes to interactively choose the images to be displayed (manual), or whether display in a predetermined sequence is desired (CINE).

Exam/study selection dialog field 37 lists the various exams which are stored relating to the patient identified in patient query dialog field 36. For example, in FIG. 2, exam/study selection dialog field 37 indicates that five examinations have been completed including a complete panorama, three intra-oral examinations including a full mouth 20-film examination (FMX-20), a 4-film bitewing (BW-4), and a 2-film bitewing (BW-2). The fifth examination is a cephalometric extraoral examination. The entry for each examination in exam/study selection dialog field 37 includes three items: examination modality, examination type, and date of examination. When different examinations are to be selected for review, fields 42, 43, 47 and 48 of patient query dialog fields 37 are updated, as appropriate, by a system user.

After a particular examination has been selected for review, the screen shown in FIG. 3 is displayed to the system user. Referring to FIG. 3, depicted are patient query dialog field 36 (displaying the same information as in field 36 of FIG. 2), icon or representation field 53, and image display fields 54. Although FIG. 3 depicts three image display fields 54, it will be understood that one or more image fields can be used. In FIG. 3, icon field 53 comprises an image of a full mouth examination 20-film holder. Within the icon in icon field 53 of FIG. 3 are film positions 56–74, each of which relate to a specific anatomical site. Specifically, position 56 is a periapical view of the right maxillary molars, position 57 is a periapical view of the right maxillary premolars, position 58 is a bitewing view of the right maxillary and mandibular molars, position 59 is a bitewing view of the right maxillary and mandibular premolars, position 60 is a periapical view of the right mandibular molars, position 61 is a periapical view of the right mandibular premolars, position 62 is a periapical view of the right maxillary canine area, position 63 is a periapical view of the right maxillary lateral incisor area, position 64 is a periapical view of the maxillary central incisor area, position 65 is a periapical view of the left maxillary lateral incisor area, position 66 is a periapical view of the left maxillary canine area, position 67 is a periapical view of the right mandibular canine area, position 68 is a periapical view of the mandibular central incisor area, position 69 is a periapical view of the left mandibular canine area, position 70 is a periapical view of the left maxillary premolars, position 71 is a periapical view of the left maxillary molars, position 72 is a bitewing view of the left maxillary and mandibular premolars, position 73 is a bitewing view of the left maxillary and mandibular molars, position 74 is a periapical view of the left mandibular premolars, and position 75 is a periapical view of the left mandibular molars.

It should be emphasized that other anatomical connotations can be applied to the various portions of the icon appearing in icon field 53, without departing from the spirit and scope of the present invention, as long as the anatomical sites represented by the icon in icon field 53 appear in normal anatomical relation to one another.

In addition, although the icon illustrated in FIG. 3 comprises an image of a full mouth examination 20-film holder, different examinations may require different icons. For example, the icon appearing in icon field 53 for a 2-film bitewing examination would be that of a 2-film holder, for example as shown in FIGS. 5A, 5B or 5C, described in more detail below.

Figure 4A:
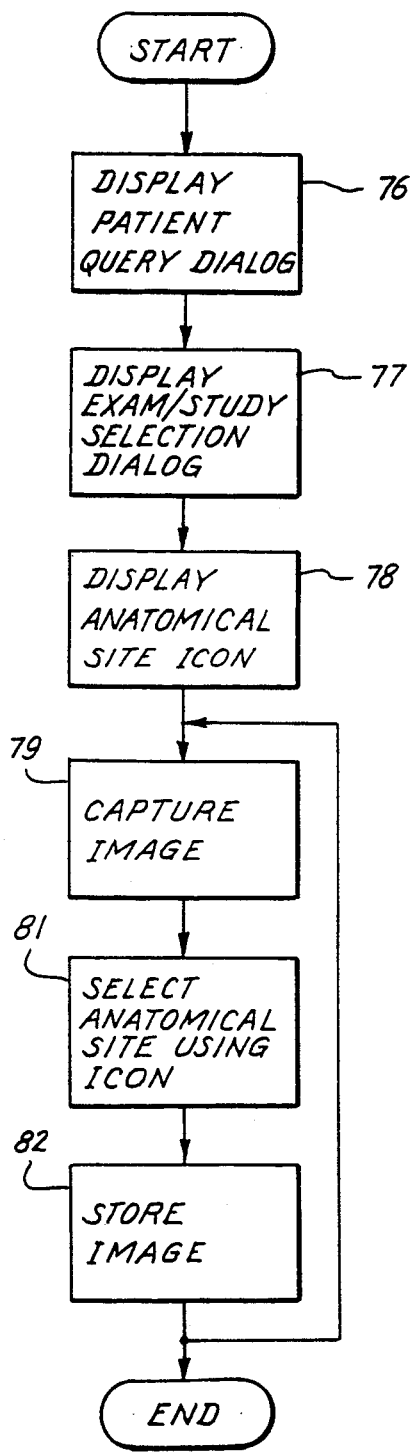
FIGS. 4A and 4B are flow charts of the method of the present invention.
Figure 4B:
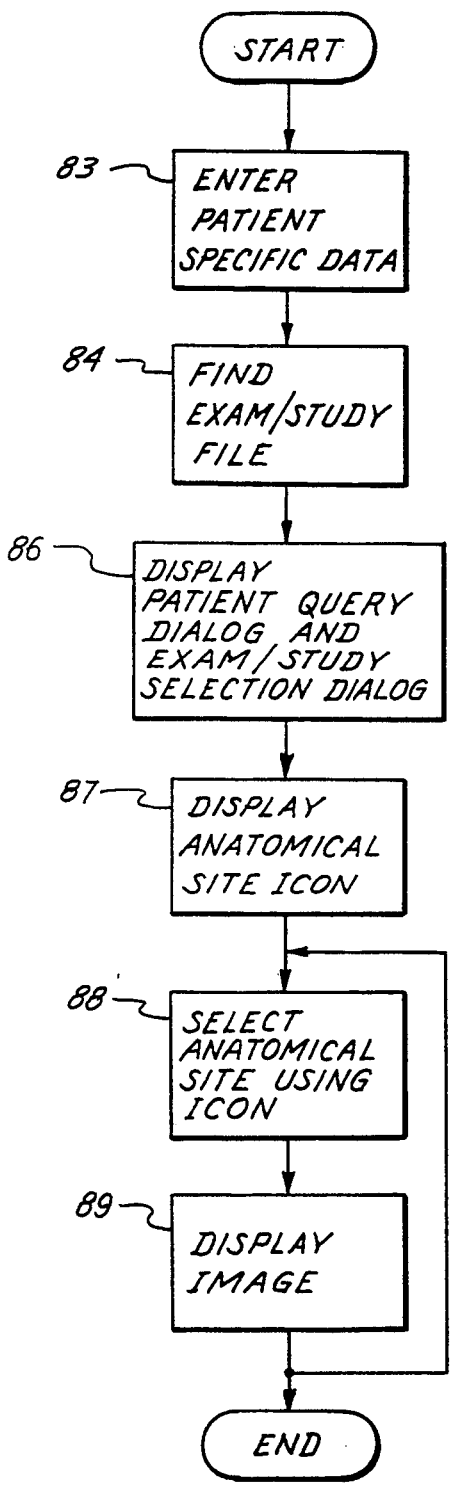

The flow charts of FIGS. 4A and 4B reveal the operation of the apparatus of FIG. 1 in combination with the display screens of FIGS. 2 and 3 to practice the method of the present invention. FIG. 4A relates to capturing and storing radiographs according to the present invention, whereas FIG. 4B relates to retrieving and displaying stored radiographs in accordance with the present invention.

Referring to FIG. 4A, after the process has begun, in block 76 a user enters patient specific data using patient query dialog field 36 shown in FIG. 2. Then, in block 76, the user enters exam/study selection data using exam/study selection dialog field 37, also shown in FIG. 2. Then, control passes to block 78 where the display of FIG. 3 is presented along with an appropriate icon in icon field 53, in accordance with the examination data entered in blocks 76 and 77. Control then passes to block 79 where, using x-ray source 33, sensor 29 and digitizer 32 (FIG. 1), an x-ray image is captured and displayed in field 54 of FIG. 3. Then, in block 86, the system user uses the icon in field 53 to select the anatomical site within icon 53 that is to be associated with the x-ray image captured in block 79. Such selection can be accomplished by use of a keyboard, mouse, touch-sensitive screen, or other functionally equivalent user input device. After the selection has occurred, control passes to block 82 where the captured image is stored along with indicia of the associated location in the icon. The steps presented in block 79, 81 and 82 are repeated until images have been captured and associated with each of the anatomical sites represented by the icon in field 53. The image capture and store process is then ended.

Referring now to FIG. 4B, the image retrieval and display process is presented. After the process is begun, a user enters patient specific data in block 83. Then, in block 84, the set of examinations associated with that patient retrieved. Control then passes to block 86 wherein the display of FIG. 2 is presented including patient specific data in field 36 and study/examination data in field 37. After a particular exam/study is selected for review by the user, control passes to block 87 where the image of FIG. 3 is presented including the appropriate icon in icon field 53. Then, in block 88, the system user selects an image to be displayed by selecting the appropriate anatomical site of the icon in icon field 53. This user selection can be by use of a keyboard, mouse, touch screen, or any other functionally similar user input device. After the particular anatomical site has been selected, control passes to block 89 where the image is displayed. The steps of blocks 88 and 89 can be repeated to display additional images from the examination selected in block 86. The image retrieval and display process is then ended.

Referring now to FIGS. 5A-S, presented are various icons of film holders that can be used in the present invention for displaying in icon field 53 (FIG. 3) to facilitate user selection of images to be displayed based on desired anatomical site.

FIGS. 5A, 5B and 5C are known as 2-film bitewings, FIGS. 5D and 5F are examples of 3-film bitewings, FIG. 5E is a 4-film bitewing, and FIGS. 5G-S are examples of full mouth surveys having various numbers of films. For each of the film holders depicted in FIGS. 5A-S, each of the film positions corresponds to a particular anatomical site within the dental arch.

FIGS. 6 and 7 are examples of different types of graphical representations of dentition that can also be used as the icon displayed in icon field 53 (FIG. 3), in accordance with the present invention. The graphical representation of FIG. 6 includes maxillary dental arch 91 and mandibular dental arch 92. The graphical representation of FIG. 7 includes a panorama of maxillary dental arch 93 and a panorama of mandibular dental arch 94. Also depicted in the graphical representation of FIG. 7 are panoramas of immature (baby teeth) maxillary and mandibular dental arches 96 and 97. Tooth numbers are also shown in the graphical representation of FIG. 7, but can be eliminated if desired.

When using the graphical representations of FIGS. 6 and 7 as icons in icon field 53 (FIG. 3), user positionable frame 98 can be displayed along with the icon and can be moved (once again by use of a keyboard, mouse, touch-sensitive screen, or functionally equivalent user input device) to select the anatomical site corresponding to the desired image to be stored or displayed.

It should be emphasized that although the present invention has been described in relation to intra-oral radiography, application to other fields of radiology is also contemplated. In addition, those of ordinary skill in this technology will appreciate that additions, deletions and changes can be made to the disclosed preferred embodiment, without departing from the scope of the invention.

APPENDIX

```
/*
 * Declaration types for callback procedures.
 */
#define DIALOG_PROC BOOL FAR PASCAL _export
#define WINDOW_PROC long FAR PASCAL _export
/*
 * Data type which defines the record which is returned from any of the
 * Get...Key() routines, and an enum that lists all the key numbers.
 */
typedef enum {
    NoKey = -1,
    IDKey = 0,
    NameKey,
    DoBKey,
    IDStudyKey = 0,
    LabelKey = 0
} KeyNumber;

typedef struct {
```

```
      KeyNumber keyNo;                              /* Number of selected key. */
      char key[256];                                /* String containing key. */
      int length;                                   /* Number of bytes in key. */
} KeyRecord, *KeyRecPtr;
/*
 * Database data types.
 */
typedef struct {
    unsigned char day;
    unsigned char month;
    unsigned short year;
} DBDate;

typedef struct {
    unsigned char hundredths;
    unsigned char seconds;
    unsigned char minutes;
    unsigned char hours;
} DBTime;

typedef enum {
    pano_mode = 0,
    intra_mode,
    extra_mode,
    ceph_mode
} Modalities;

typedef enum {
    complete_type = 0,
    fmx20_type = 0,
    fmx14_type,
    bw4_type,
    bw2_type
} ExamTypes;
/*
 * Database record structures.
 */
#define CHART_LEN 20
#define NAME_LEN 20
#define MAX_COMMENT (2048)

typedef struct {
    char chart_number[CHART_LEN];
    short modality;
    short exam_type;
    DBDate date_of_exp;
} StudyKey, FAR *StudyKeyPtr;

typedef struct {
    char chart_number[CHART_LEN];        /* Patient's chart number. */
    char key_first_name[NAME_LEN];       /* First name in a form that allows for
                                            case-insensitive lookups. */
    char key_middle_name[NAME_LEN];      /* Middle name case-insensitive. */
    char key_last_name[NAME_LEN];        /* Last name case-insensitive. */
    DBDate date_of_birth;                /* Patient's date of birth. */
    char first_name[NAME_LEN];           /* First name as entered by user. */
    char middle_name[NAME_LEN];          /* Middle name. */
    char last_name[NAME_LEN];            /* Last name. */
} PatientRecord, FAR *PatientPtr;

typedef struct {
    char chart_number[CHART_LEN];        /* Patient's chart number. */
    short modality;                      /* Study modality. Integer from enum. */
    short exam_type;                     /* Type of exam. Integer from enum. */
    DBDate date_of_exp;                  /* Date of examination. */
    DBTime time_of_exp;                  /* Time of examination. */
    short x_size;                                    /* X dimension of study i
        short y_size;                    /* Y size of images. */
    char referring_service[NAME_LEN];    /* Name of referring service. */
    char referring_doctor[NAME_LEN];     /* Name of referring doctor. */
    char image_file[13];                 /* Image filename. */
```

```c
    char disk_label[13];              /* Label of disk in which image file is s
    short status;                     /* Interpretation status. Integer from en
    char comments[MAX_COMMENT];       /* Comments. Variable length. */
} StudiesRecord, FAR *StudiesPtr;

typedef struct {
    char disk_label[13];
    unsigned long last_file;
    unsigned long capacity;
    unsigned long volume;
} DiskRecord, FAR *DiskPtr;

typedef enum {
    portrait  = TRUE,
    landscape = FALSE
} Orientations;

typedef struct {
    POINT corner;                     /* Position of upper-left corner (in mm) */
    BOOL  portrait;                   /* x-ray is oriented portrait in holder. */
} ImageInfo, NEAR *ImageInfoPtr;

typedef struct {
    char far *name;                   /* Name to be displayed. */
    int numImages;                    /* Number of images in study. */
    short mmWidth;                    /* Width of holder in mm. */
    short mmHeight;                   /* Height of holder in mm. */
    ImageInfo images[24];             /* Data for each image in holder. */
} ModeInfo, NEAR *ModeInfoPtr;

typedef enum {
    January=0, February, March, April, May, June, July,
    August, September, October, Novenber, December
} monthEnum;

typedef unsigned char far *ImagePtr;
/*
 * Global data.  Most global variable names begin with the letter 'g'.
 */
#ifndef EXTERN
define EXTERN extern EXTERN char *gAppName;

EXTERN char *month_names[12];
EXTERN char *month_abbrs[12];
EXTERN int month_days[12];

EXTERN char far *mode_strings[];

EXTERN ModeInfo pano_modes[];
EXTERN ModeInfo intra_modes[];

EXTERN char far *interp_strings[];
#else
/*
 * The application name.
 */
char *gAppName = "WDPX";
/*
 * Stuff for converting dates.
 */
char *month_names[12] = {
    "January", "February", "March", "April", "May", "June",
    "July", "August", "September", "October", "November", "December"
};
char *month_abbrs[12] = {
    "Jan", "Feb", "Mar", "Apr", "May", "Jun",
    "Jul", "Aug", "Sep", "Oct", "Nov", "Dec"
};
int month_days [12] = { 31, 28, 31, 30, 31, 30, 31, 31, 30, 31, 30, 31 };
```

```c
/*
 * Strings which appear in the modality, exam type, and interpretation
 * status drop-down boxes.
 */
char far *mode_strings[] = {
    "Panoramic",
    "Intraoral",
    "Extraoral",
    "Cephalometric",
    0
};

ModeInfo pano_modes[] = {
    { "Complete", 1, 0,   0 },
    { 0, 0, 0, 0 }
};

ModeInfo intra_modes[] = {
    { "FMX(20)", 20, 345, 124,
        {
                { (   4,  10 ), landscape },
                { (  49,  10 ), landscape },
                { (   4,  48 ), landscape },
                { (  49,  48 ), landscape },
                { (   4,  87 ), landscape },
                { (  49,  87 ), landscape },
                { ( 100,  17 ), portrait  },
                { ( 130,  17 ), portrait  },
                { ( 160,  17 ), portrait  },
                { ( 190,  17 ), portrait  },
                { ( 220,  17 ), portrait  },
                { ( 130,  70 ), portrait  },
                { ( 160,  70 ), portrait  },
                { ( 190,  70 ), portrait  },
                { ( 257,  10 ), landscape },
                { ( 301,  10 ), landscape },
                { ( 257,  48 ), landscape },
                { ( 301,  48 ), landscape },
                { ( 257,  87 ), landscape },
                { ( 301,  87 ), landscape }
        }
    },
    { "FMX(14)", 14, 290, 108,
        {
                { (   3,  14 ), landscape },
                { (  49,  14 ), landscape },
                { (   3,  66 ), landscape },
                { (  49,  66 ), landscape },
                { (  94,   8 ), portrait  },
                { ( 130,   8 ), portrait  },
                { ( 165,   8 ), portrait  },
                { (  94,  61 ), portrait  },
                { ( 130,  61 ), portrait  },
                { ( 165,  61 ), portrait  },
                { ( 201,  14 ), landscape },
                { ( 247,  14 ), landscape },
                { ( 201,  66 ), landscape },
                { ( 247,  66 ), landscape }
        }
    },
    { "BW(4)",   4, 191,  70,
        {
                { (   8,  23 ), landscape },
                { (  52,  23 ), landscape },
                { (  98,  23 ), landscape },
                { ( 142,  23 ), landscape }
        }
    },
    { "BW(2)",   2, 102,  70,
        {
                { (   9,  22 ), landscape },
                { (  54,  22 ), landscape }
```

```
    }
},
{ 0, 0, 0, 0 }
};

char far *interp_strings[] = {
    "Pending",
    "Complete",
    0
};
#endif

EXTERN PatientPtr gPatient;

EXTERN HWND gInst;                  /* Global copy of current instance of app. */
EXTERN KeyRecord gKey;              /* Global pointer to a key record. Used to
                                       simplify communication between database
                                       dialog callback functions. */
EXTERN HWND gMainWindow;            /* Handle to the main window. */
EXTERN HWND gPatDlg;                /* Handle to the non-modal dialog which
                                       displays the information about the
                                       current patient and image set. */
EXTERN HWND gCommentWnd;            /* Handle to the comments entry window. */
EXTERN HWND gTemplateWnd;           /* Handle to the template window. */
EXTERN HANDLE ghPatient;            /* Global patient record used by dialog
                                       callback routines. */
EXTERN BOOL gIsAPatient;            /* Is there a patient record in gPatient? */
EXTERN HANDLE ghStudy;              /* Global studies record used by dialog
                                       callback routines. */
EXTERN BOOL gIsAStudy;              /* Is there a study record in gStudy? */
EXTERN HANDLE ghDisk;               /* Global disks database record. */
EXTERN char gOpenName[132];         /* Global filename buffer. The result of
                                       calling the GetFile dialog is placed in
                                       this buffer. */
EXTERN char gPatPB[128];            /* Patient file position block. */
EXTERN char gStudyPB[128];          /* Study file position block. */
EXTERN char gDiskPB[128];           /* Disk file position block. */

EXTERN HWND gImageWnd;              /* Handle to the currently active image
                                       window. */
EXTERN HWND gResultsWnd;            /* Handle to the results window. */
EXTERN HANDLE ghDIB;                /* Handle to a 256-gray DIB. */
EXTERN HBRUSH ghChildBrush;         /* Handle to the brush used to paint the
                                       template child windows. */
EXTERN HPALETTE gPalette;           /* Handle to palette containing gray levels. *
/*
 * About.c
 *
 * This source file contains the callback routine for the About box dialog.
 *
 * Change log
 *      04/15/91 - CDW - Added WM_INITDIALOG processing to center box on
 *                       monitor.
 */
#include "windows.h"
#include "btrieve.h"
#include "wdpx.h"
#include "resource.h"
#include "wdpxdlg.h"
#pragma hdrstop
#include "about.h"
/*
 * About
 *
 * This is the callback for the about box.
 */
DIALOG_PROC About(HWND dlg, WORD msg, WORD wP, DWORD lP) {
    BOOL retVal = FALSE;
    RECT rect;
    int xScreen, yScreen, width, height;
```

```
      switch (msg) {
      case WM_INITDIALOG:
          xScreen = GetSystemMetrics(SM_CXSCREEN);
          yScreen = GetSystemMetrics(SM_CYSCREEN);
          GetWindowRect(dlg, &rect);
          width  = rect.right - rect.left;
          height = rect.bottom - rect.top;
          MoveWindow(dlg, (xScreen-width)/2,
                          (yScreen-height)/2,
                          width,
                          height,
                          FALSE);

retVal = TRUE;
          break;
      case WM_COMMAND:
          if (wP == IDOK || wP == IDCANCEL) {
              EndDialog(dlg, TRUE);
              retVal = TRUE;
          } /* if */
          break;
      } /* switch */ return retVal;
  } /* About */
/*
 * AutoWnd.c
 *
 * This source file contains the callback routine for the windows which are
 * used to display the images when in automatic mode.  This same window is
 * used to display panoramic x-rays.
 *
 * Change log
 *     04/09/91 - CDW - Created and debugged originally.
 *     05/03/91 - CDW - Changed so that window would only use the available
 *                     space under the ptd dialog.
 */
#include "windows.h"
#include "btrieve.h"
#include "wdpx.h"
#include "resource.h"
#include "wdpxdlg.h"
#pragma hdrstop
#include "study.h"
#include "autownd.h"
#include "studydb.h"
#include "messages.h"
/*
 * SizeTheWindow
 *
 * This local routine does all the work involved in sizing the window in the
 * open area under the patient display dialog box, taking the study type and
 * image orientation into account.
 */
static void SizeTheWindow(HWND wnd, StudiesPtr s, int which) {
    int width, height;
    int screenX, screenY;
    int borderX, borderY;
    int nX, nY, nW, nH;
    RECT ptdRect;
    /*
     * First, we take the exam type into account to compute the expected width
     * and height of the image.
     */
    GetStudyDimensions(s, which, &width, &height);
    /*
     * Some metrics we can use here.
     */
    borderX = GetSystemMetrics(SM_CXBORDER);
    borderY = GetSystemMetrics(SM_CYBORDER);
```

```
    width  += 2 * borderX;
    height += 2 * borderY;
    /*
     * Center the image horizontally in the space available.
     */
    screenX = GetSystemMetrics(SM_CXSCREEN);
    if (width > screenX) {
        nX = 0;
        nW = screenX;
    } else {
        nX = (screenX-width) / 2;
        nW = width;
    } /* if */
    /*
     * Center the image vertically, making sure not to overrun into the
     * patient display.
     */
    GetWindowRect(gPatDlg, &ptdRect);
    screenY = GetSystemMetrics(SM_CYSCREEN);

if ((screenY - height) < ptdRect.bottom) {
        nY = ptdRect.bottom;
        nH = screenY-nY;
    } else {
        nY = ptdRect.bottom + (screenY-ptdRect.bottom-height) / 2;
        nH = height;
    } /* if */
    /*
     * And now actually move the window.
     */
    MoveWindow(wnd, nX, nY, nW, nH, FALSE);
} /* SizeTheWindow */
/*
 * ChangeImage
 *
 * Local routine to change the image which is being displayed.  This routine
 * does not do the painting, just updates the information and invalidates
 * the window.
 */
static void ChangeImage(HWND wnd, StudiesPtr s, int old, int new) {
    RECT winRect;
    /*
     * Store the new selected image in the window.
     */
    SetWindowWord(wnd, 2, new);
    /*
     * Resize the image if the orientation changes.
     */
    if (intra_modes[s->exam_type].images[old].portrait !=
        intra_modes[s->exam_type].images[new].portrait)     {
        SizeTheWindow(wnd, s, new);
    } /* if */
    /*
     * Have the whole thing redrawn.
     */
    GetClientRect(wnd, &winRect);
    InvalidateRect(wnd, &winRect, FALSE);
} /* ChangeImage */
/*
 * AutomaticWindow
 *
 * This is the main callback routine for the window which is used to display
 * automatic images.
 */
WINDOW_PROC AutomaticWindow(HWND wnd, WORD msg, WORD wP, LONG lP) {
    LONG retVal = NULL;
    HDC hDC;
    char huge *theBits;
    HANDLE hBits;
    RECT winRect;
```

```
PAINTSTRUCT ps;
LPBITMAPINFO theDib;
long which;
StudiesPtr s;
int newSelected, oldSelected;
int width, height, srcY, srcX;

switch (msg) {
case WM_CREATE:
    /*
     * When the window is created, we need to size it appropriately for
     * the first image.
     */
    s = (StudiesPtr)GlobalLock(ghStudy);
    SizeTheWindow(wnd, s, 0);
    GlobalUnlock(ghStudy);
    break;
case WM_DESTROY:
    break;
case WM_PAINT:
    /*
     * Lock the bits handle.
     */
    hBits   = (HANDLE)GetWindowWord(wnd, 0);
    theBits = GlobalLock(hBits);
    /*
     * Lock the DIB handle.
     */
    theDib = (LPBITMAPINFO)GlobalLock(ghDIB);
    /*
     * The index for this window is stored in the second extra word.  Use
     * it to compute the index into the data.
     */
    s = (StudiesPtr)GlobalLock(ghStudy);
which = (long)GetWindowWord(wnd, 2);
theBits += which*s->x_size*s->y_size;
/*
 * Get a display context.
 */
hDC = BeginPaint(wnd, &ps);
/*
 * Get the palette here.
 */
SelectPalette(hDC, gPalette, 0);
RealizePalette(hDC);
/*
 * We need the dimensions of the client area of the window.
 */
GetClientRect(wnd, &winRect);
/*
 * Compute the height of the bitmap to be displayed, to make sure
 * that it is centered in the available space.
 */
GetStudyDimensions(s, which, &width, &height);
if (width > winRect.right) {
    srcX = (width - winRect.right) / 2;
} else {
    srcX = 0;
} /* if */ if (height > winRect.bottom) {
    srcY = (height - winRect.bottom) / 2;
} else {
    srcY = 0;
} /* if */
/*
 * Set the dimension of the DIB.
 */
theDib->bmiHeader.biWidth  = width;
theDib->bmiHeader.biHeight = height;
/*
```

```
     * Display the bitmap.
     */
    StretchDIBits(hDC,
                0,
                0,
                winRect.right,
                winRect.bottom,
                srcX,
                srcY,
                winRect.right,
                winRect.bottom,
                (LPSTR)theBits,
                theDib,
                    DIB_RGB_COLORS,
                    SRCCOPY);
    /*
     * Clean up.
     */
    GlobalUnlock(ghStudy);
    GlobalUnlock(ghDIB);
    GlobalUnlock(hBits);
    EndPaint(wnd, &ps);
    break;
case WM_CHAR:
    /*
     * On a space bar, we want to advance the image.  Otherwise, fall
     * through to the mouse down code.
     */
    if (wP != ' ')
        break;
case WM_LBUTTONDOWN:
    /*
     * First, get the current image number from the extra area, and
     * compute the new selected image.
     */
    s = (StudiesPtr)GlobalLock(ghStudy);
    oldSelected = GetWindowWord(wnd, 2);
    newSelected = (oldSelected+1)%NumImages(s);
    if (s->modality == intra_mode) {
        /*
         * Notify the template window, which will control the changing of
         * the image.
         */
        PostMessage(gTemplateWnd, DPX_ChangeImage, newSelected, 0);
    } /* if */
    GlobalUnlock(ghStudy);
    break;
case DPX_ChangeImage:
    s = (StudiesPtr)GlobalLock(ghStudy);
    ChangeImage(wnd, s, GetWindowWord(wnd, 2), wP);
    GlobalUnlock(ghStudy);
    break;
default:
    retVal = DefWindowProc(wnd, msg, wP, lP);
    break;
} /* switch */ return retVal;
} /* AutomaticWindow */
/*
 * ManImage.c
 *
 * This file contains the callback routine for the window which is used to
 * display images in manual mode.  This window has a caption and can be
 * resized.  When the window is not large enough for the whole image, then
 * scroll bars are shown to allow the user to view different portions of the
 * image.
 *
 * Change log
 *      04/15/91 - CDW - Changed to use built-in scroll bars.
```

```c
*/
#include "windows.h"
#include "btrieve.h"
#include "wdpx.h"
#include "resource.h"
#include "wdpxdlg.h"
#pragma hdrstop
#include "study.h"
#include "manimage.h"
#include "messages.h"
/*
 * AdjustScrollBars
 *
 * Local routine to resize and adjust the scroll bars when the window is
 * resized.
 */
static void AdjustScrollBars(HWND wnd, DWORD lP) {
    int newX, newY;
    int xvScroll, yhScroll;
    long which;
    StudiesPtr s;
    int x_size, y_size;
    RECT rect;
    int oldMin, oldMax;
    /*
     * First, get the system metrics for scroll bars.
     */
    xvScroll = GetSystemMetrics(SM_CXVSCROLL);
    yhScroll = GetSystemMetrics(SM_CYHSCROLL);
    /*
     * Extract the new height and width of the window from the message.
     */
    newX = LOWORD(lP);
    newY = HIWORD(lP);
    /*
     * The index for this window is stored in the second extra word.  We
     * need to get the size of intraoral images in this study so that we can
     * decide whether or not to show the scroll bars.
     */
which = (long)GetWindowWord(wnd, 0);
s = (StudiesPtr)GlobalLock(ghStudy);
GetStudyDimensions(s, which, &x_size, &y_size).
GlobalUnlock(ghStudy);
/*
 * All set, now for the real purpose for this work.  If the visibility of
 * the scroll bars changes, we need only reset the ranges of the scroll
 * bars.  This will trigger a new WM_SIZE message.  If the visibility
 * does not change, then we can invalidate the window to cause the re-
 * display of the image.  The first thing to do it find out if the scroll
 * bars are currently visible, since this affects the computation of
 * whether they ought to be visible as a result of resizing the window.
 */
GetScrollRange(wnd, SB_HORZ, &oldMin, &oldMax);
if (oldMin == oldMax) {
    /*
     * The scroll bars are currently not visible, so the client region
     * is the entire area inside the borders.  Check to see if that is
     * enought space in which to display the entire image.
     */
    if (newX < x_size || newY < y_size) {
        int newMax;
        /*
         * Scroll bars need to be shown.  Start with the horizontal since
         * we already have its range.
         */
        newMax = x_size - newX + xvScroll - 1;
        SetScrollRange(wnd, SB_HORZ, 0, newMax, FALSE);
        SetScrollPos(wnd, SB_HORZ, 0, FALSE);
        /*
         * Now for the vertical scroll bar.
         */
```

```
            GetScrollRange(wnd, SB_VERT, &oldMin, &oldMax);
            newMax = y_size - newY + yhScroll - 1;
            SetScrollRange(wnd, SB_VERT, 0, newMax, FALSE);
            SetScrollPos(wnd, SB_VERT, 0, FALSE);
        } else {
            /*
             * The scroll bars can remain invisible.  Just cause the image to
             * be redrawn.
             */
            GetClientRect(wnd, &rect);
            InvalidateRect(wnd, &rect, FALSE);
        } /* if */
    } else {
        /*
         * Since the scroll bars are currently visible, the client rectangle
         * excludes the space for the scroll bars.  To determine if the
         * window is big enough for the whole image, we need to add in the
         * area of the scroll bars.
         */
        if (newX+xvScroll < x_size || newY+yhScroll < y_size) {
            int newMax;
            int hPos, vPos;
            /*
             * This window will still not be large enough for the whole image,
             * so we should invalidate the current client area and let the
             * partial image be redrawn.
             */
            GetClientRect(wnd, &rect);
            InvalidateRect(wnd, &rect, FALSE);
            /*
             * Now rescale the scroll bars.  We can start with the horizontal
             * since we already have its range.
             */
            newMax = x_size - newX - 1;
            hPos   = GetScrollPos(wnd, SB_HORZ);
            if (oldMax != newMax) {
                SetScrollRange(wnd, SB_HORZ, 0, newMax, FALSE);
                if (hPos > newMax) hPos = newMax;
            } /* if */
            /*
             * Now for the vertical scroll bar.
             */
            GetScrollRange(wnd, SB_VERT, &oldMin, &oldMax);
            vPos   = GetScrollPos(wnd, SB_VERT);
            newMax = y_size - newY - 1;
            if (oldMax != newMax) {
                SetScrollRange(wnd, SB_VERT, 0, newMax, FALSE);
                if (vPos > newMax) vPos = newMax;
            } /* if */
            /*
             * Now reset the scroll bar positions.  Redraw the scroll bars
             * now.
             */
            SetScrollPos(wnd, SB_HORZ, hPos, TRUE);
            SetScrollPos(wnd, SB_VERT, vPos, TRUE);
        } else {
            /*
             * The new window will be large enough for the whole image.  We
             * can therefore hide the scroll bars.
             */
            SetScrollRange(wnd, SB_VERT, 0, 0, FALSE);
            SetScrollRange(wnd, SB_HORZ, 0, 0, FALSE);
        } /* if */
    } /* if */
} /* AdjustScrollBars */
/*
 * ScrollImage
 *
 * Local routine to adjust the image position when the user clicks in the
 * scrollbars.
 */
```

```
static void ScrollImage(HWND wnd, int which, WORD wP, DWORD lP) {
    int newPos, sMin, sMax, oldPos;
    RECT rect;

GetScrollRange(wnd, which, &sMin, &sMax);
    newPos = oldPos = GetScrollPos(wnd, which);

switch (wP) {
    case SB_BOTTOM:
        newPos = sMax;
        break;
    case SB_LINEDOWN:
        if (oldPos < sMax)
            newPos = oldPos + 1;
        break;
    case SB_LINEUP:
        if (oldPos > sMin)
            newPos = oldPos - 1;
        break;
    case SB_PAGEDOWN:
        newPos = oldPos + 16;
        if (newPos > sMax)
            newPos = sMax;
        break;
    case SB_PAGEUP:
        newPos = oldPos - 16;
        if (newPos < sMin)
            newPos = sMin;
        break;
    case SB_THUMBPOSITION:
        newPos = LOWORD(lP);
        break;
    case SB_TOP:
        newPos = sMin;
        break;
    } /* switch */
    /*
     * If the click caused the image to scroll, invalidate the image to get
     * it redrawn.
     */
    if (newPos != oldPos) {
        SetScrollPos(wnd, which, newPos, TRUE);
        GetClientRect(wnd, &rect);
        InvalidateRect(wnd, &rect, FALSE);
    } /* if */
} /* ScrollImage */
/*
 * ManualImageWindow
 *
 * This is the main callback routine for the window which is used to display
 * image in manual windows.
 */
WINDOW_PROC ManualImageWindow(HWND wnd, WORD msg, WORD wP, LONG lP) {
    LONG retVal = NULL;
    LPBITMAPINFO theDib;
    HANDLE hBits;
    char huge *theBits;
    HDC hDC;
    PAINTSTRUCT ps;
    LPPOINT rgpt;
    POINT pt;
    RECT rect;
    long which;
    StudiesPtr s;
    int x_size, y_size;
    HWND owner;
    int X, Y;
    int sMin, sMax;

switch (msg) {
    case WM_CREATE:
```

```
/*
 * Make sure that the ranges for the 2 scroll bars are 0, thereby
 * making them "already invisible".
 */
    SetScrollRange(wnd, SB_HORZ, 0, 0, FALSE);
    SetScrollRange(wnd, SB_VERT, 0, 0, FALSE);
    break;
case WM_PAINT:
    /*
     * The index for this window is stored in the second extra word.
     */
    which = (long)GetWindowWord(wnd, 0);
    /*
     * Get the x and y sizes from the study record.
     */
    s = (StudiesPtr)GlobalLock(ghStudy);
    GetStudyDimensions(s, which, &x_size, &y_size);
    GlobalUnlock(ghStudy);
    /*
     * Lock the bits handle.
     */
    hBits  = (HANDLE)GetClassWord(wnd, 0);
    theBits = GlobalLock(hBits);
    /*
     * Lock the DIB handle.
     */
    theDib = (LPBITMAPINFO)GlobalLock(ghDIB);
    /*
     * Use the index and dimension information to compute the offset into
     * the data.
     */
    theBits += which*x_size*y_size;
    /*
     * Get a display context.
     */
    hDC = BeginPaint(wnd, &ps);
    /*
     * Get the palette here.
     */
    SelectPalette(hDC, gPalette, 0);
    RealizePalette(hDC);
    /*
     * Determine the extent of the image area. We compute the portion of
     * the bitmap that is visible here.
     */
    GetClientRect(wnd, &rect);
    GetScrollRange(wnd, SB_HORZ, &sMin, &sMax);
    if (sMin != sMax) {
        /*
         * The scroll bars are visible, so only part of the image shows.
         * The x and y coordinates of the portion of the image that needs
         * to be displayed are the current values of the scroll bars.
         */
        X = GetScrollPos(wnd, SB_HORZ);
        Y = GetScrollPos(wnd, SB_VERT);
    } else {
        /*
         * Since neither scroll bar is visible, the window is displaying
         * the entire image.
         */
        X = 0;
        Y = 0;
    } /* if */
    /*
     * Display the bitmap.
     */
    theDib->bmiHeader.biWidth  = x_size;
    theDib->bmiHeader.biHeight = y_size;
    SetDIBitsToDevice(hDC,                     /* The device context */
                      -X,                      /* x origin of destination */
                      -Y,                      /* y origin of destination */
```

```
                          x_size,              /* x extent of DIB rect */
                          y_size,              /* y extent of DIB rect */
                          0,                   /* x origin of source */
                          0,                   /* y origin of source */
                          0,                   /* starting scan line */
                          y_size,              /* number of scan lines */
                          (LPSTR)theBits,      /* the bits */
                          theDib,              /* the DIB */
                          DIB_RGB_COLORS);     /* color usage */
        /*
         * Clean up.
         */
        GlobalUnlock(ghDIB);
        GlobalUnlock(hBits);
        EndPaint(wnd, &ps);
        break;
    case WM_SIZE:
        if (wP == SIZENORMAL && IsWindowVisible(wnd))
            AdjustScrollBars(wnd, lP);
        break;
    case WM_SYSCOMMAND:
        if (wP == SC_MINIMIZE || wP == SC_ICON) {
            /*
             * Whenever the window is minimized, the template holder window
             * corresponding to this window should be re-drawn.
             */
            ShowWindow(wnd, SW_HIDE);
            owner = GetDlgItem(gTemplateWnd, GetWindowWord(wnd, 0));
            GetClientRect(owner, &rect);
            InvalidateRect(owner, &rect, FALSE);
        } else if (wP == SC_MAXIMIZE || wP == SC_ZOOM) {
            POINT rgpt[5];
            RECT rect;
            /*
             * When the window is maximized, we need to resize the window
             * to its maximum size.  Send the window a WM_GETMINMAXINFO
             * message to get the maximum size.
             */
            SendMessage(wnd, WM_GETMINMAXINFO, 0, (LONG)rgpt);
            /*
             * Now size the window appropriately.
             */
            GetWindowRect(wnd, &rect);
            MoveWindow(wnd, rect.left,
                            rect.top,
                            rgpt[4].x,
                            rgpt[4].y,
                            TRUE);
        } else {
            retVal = DefWindowProc(wnd, msg, wP, lP);\
        } /* if */
        break;
    case WM_GETMINMAXINFO: {
        int xVScroll, xFrame, yHScroll, yFrame, yCaption;
        /*
         * The index for this window is stored in the second extra word.
         */
        which = (long)GetWindowWord(wnd, 0);
        /*
         * Get the x and y sizes from the study record.
         */
        s = (StudiesPtr)GlobalLock(ghStudy);
        GetStudyDimensions(s, which, &x_size, &y_size);
        GlobalUnlock(ghStudy);
        /*
         * Cast lP into the correct type.
         */
        rgpt = (LPPOINT)lP;
        /*
         * Get the needed system metrics.
```

```
         */
        xVScroll = GetSystemMetrics(SM_CXVSCROLL);
        yHScroll = GetSystemMetrics(SM_CYHSCROLL);
        xFrame   = GetSystemMetrics(SM_CXFRAME);
        yFrame   = GetSystemMetrics(SM_CYFRAME);
        yCaption = GetSystemMetrics(SM_CYCAPTION);
        /*
         * Compute the minimum tracking size:
         *      width:  CXVSCROLL + 2*CXFRAME + 128
         *      height: CYHSCROLL + 2*CYFRAME-1 + CYCAPTION + 128
         */
        pt.x = xVScroll + 2*xFrame + 128;
        pt.y = yHScroll + 2*yFrame-1 + yCaption + 128;
        rgpt[3] = pt;
        /*
         * Compute the maximum tracking size, which is the size of the
         * original image:
         *      width:  2*CXFRAME + x_size
         *      height: 2*CYFRAME-1 + CYCAPTION + y_size
         */
        pt.x = 2*xFrame + x_size;
        pt.y = 2*yFrame-1 + yCaption + y_size;
        rgpt[4] = pt;
        break;
        }
    case WM_VSCROLL:
        if (wP != SB_ENDSCROLL && wP != SB_THUMBTRACK)
            ScrollImage(wnd, SB_VERT, wP, lP);
        break;
    case WM_HSCROLL:
        if (wP != SB_ENDSCROLL && wP != SB_THUMBTRACK)
            ScrollImage(wnd, SB_HORZ, wP, lP);
        break;
    default:
        retVal = DefWindowProc(wnd, msg, wP, lP);
        break;
    } /* switch */ return retVal;
} /* TemplateWindow */
#include "windows.h"
#include "btrieve.h"
#include "wdpx.h"
#include "resource.h"
#include "wdpxdlg.h"
#pragma hdrstop
#include "study.h"
#include "acquire.h"
#include "studydb.h"

#include <string.h>
#include <io.h>
#include <fcntl.h>
include <sys\stat.h> define BYTES_PER_IO 32768
/*
 * StudySpaceRequirements
 *
 * This routine computes the amount of disk space required by a study.
 */
unsigned long StudySpaceRequirements(HANDLE hStudy) {
    return AcquireSize(hStudy);
} /* StudySpaceRequirements */
/*
 * ExistingStudySize
 *
 * This routine returns the amount of memory required to read an existing
 * study from disk.
 */
```

```c
unsigned long ExistingStudySize(HANDLE hStudy) {
    StudiesPtr s;
    unsigned long space;

s = (StudiesPtr)GlobalLock(hStudy);

space = NumImages(s);
    space = space * s->x_size * s->y_size;

GlobalUnlock(hStudy);

return space;
} /* ExistingStudySize */
/*
 * SaveStudy
 *
 * This routine manages the file I/O needed to store a study to disk.
 */
BOOL SaveStudy(HANDLE hStudy, HANDLE data) {
    StudiesPtr s = (StudiesPtr)GlobalLock(hStudy);
    char fullFilename[16];
    int f;
    char drive[2];
    HCURSOR oldCursor;
    /*
     * This could take a while, display the hourglass cursor.
     */
    oldCursor = SetCursor(LoadCursor(NULL, IDC_WAIT));
    /*
     * Get the drive name from the initialization file.
     */
    GetProfileString(gAppName, "Image Drive", "G", drive, 2);
    /*
     * Now, we need to create the filename for the image file.
     */
    lstrcpy(fullFilename, drive);
    lstrcat(fullFilename, ":\\");
    lstrcat(fullFilename, s->image_file);
    /*
     * Now, open the file.
     */
    f = open(fullFilename, O_RDWR|O_CREAT|O_BINARY, S_IREAD|S_IWRITE);
    /*
     * Now write out the data.
     */
    /*
     * Clean up.
     */
    close(f);
    SetCursor(oldCursor);
    GlobalUnlock(hStudy);
    return TRUE;
} /* SaveStudy */
/*
 * LoadStudy
 *
 * This routine manages the file I/O needed to retrieve a stored study from
 * disk.
 */
BOOL LoadStudy(HANDLE hStudy, HANDLE buffer) {
    StudiesPtr theStudy;
    unsigned char huge *pB;
    int file;
    char fullFilename[16];
    unsigned bytesRead;
    char drive[2];
    long bytesToRead;
    HCURSOR oldCursor;
    /*
     * This could take a while, display the hourglass cursor.
```

```
        */
        oldCursor = SetCursor(LoadCursor(NULL, IDC_WAIT));
        /*
         * Get the drive name from the initialization file.
         */
        GetProfileString(gAppName, "Image Drive", "G", drive, 2);
        /*
         * Lock the handles.
         */
        theStudy = (StudiesPtr)GlobalLock(hStudy);
        pB = GlobalLock(buffer);
        /*
         * Open the file for the study.
         */
        lstrcpy(fullFilename, drive);
        lstrcat(fullFilename, ":\\");
        lstrcat(fullFilename, theStudy->image_file);
        file = open(fullFilename, O_RDONLY);
        /*
         * Read in the file.
         */
        bytesToRead = (long)theStudy->x_size *
                      (long)theStudy->y_size *
                      (long)NumImages(theStudy);

bytesRead = _lread(file, (LPSTR)pB, BYTES_PER_IO);
        bytesToRead -= BYTES_PER_IO;
        while (bytesToRead > 0 && bytesRead == BYTES_PER_IO) {
            pB += BYTES_PER_IO;
            bytesRead = _lread(file, (LPSTR)pB, BYTES_PER_IO);
            bytesToRead -= BYTES_PER_IO;
        } /* while */
        /*
         * All done.
         */
        close(file);
        GlobalUnlock(buffer);
        GlobalUnlock(hStudy);
        SetCursor(oldCursor);

return TRUE;
} /* LoadStudy */
/*
 * HideStudyWindows
 *
 * This routine destroys any windows which have been opened to display
 * images.
 */
void HideStudyWindows(void) {
    if (gImageWnd != 0) {
        DestroyWindow(gImageWnd);
        gImageWnd = 0;
    } /* if */
} /* HideStudyWindows */
/*
 * DisplayStudyWindows
 *
 * This routine opens and displays the windows used to display images for
 * the current study.  It uses the global study record.  The window sizes
 * itself in the WM_CREATE case.
 */
void DisplayStudyWindows(HANDLE hData) {
    HWND hWnd;
    /*
     * Create the window and display it.
     */
    hWnd = CreateWindow("autoWClass",
                        NULL,
                        WS_BORDER | WS_POPUP,
                        0,
                        0,
```

```
                        0,
                        0,
                        gMainWindow,
                        NULL,
                        gInst,
                        NULL
                        );
    SetWindowWord(hWnd, 0, hData);
    SetWindowWord(hWnd, 2, 0);
    ShowWindow(hWnd, SW_SHOW);
    UpdateWindow(hWnd);
    gImageWnd = hWnd;
} /* DisplayStudyWindows */
/*
 * UpdateStudyWindow
 *
 * This routine causes the indicated window to be updated from new data.
 */
void UpdateStudyWindow(void) {
    InvalidateRect(gImageWnd, NULL, FALSE);
} /* UpdateStudyWindow */
/*
 * GetStudyDimensions
 *
 * This routine encapsultates all the computation necessary to determine
 * the width and height of an image in a study.
 */
void GetStudyDimensions(StudiesPtr s, int which, int *width, int *height) {
    switch (s->modality) {
    case pano_mode:
        *width  = s->x_size;
        *height = s->y_size;
        break;
    case intra_mode:
        if (intra_modes[s->exam_type].images[which].portrait) {
            *width  = s->x_size;
            *height = s->y_size;
        } else {
            *width  = s->y_size;
            *height = s->x_size;
        } /* if */
        break;
    } /* switch */
} /* GetStudyDimensions */
#include "windows.h"
#include "btrieve.h"
#include "wdpx.h"
#include "resource.h"
#include "wdpxdlg.h"
#pragma hdrstop
#include "tmplchld.h"
#include "messages.h"
#include "manimage.h"
/*
 * Local variables used when dragging the outline of a window which will be
 * used to display the image when the user releases the mouse.
 */
static BOOL captured;           /* Is mouse captured to display rect? */
static RECT dragRect;           /* Rectangle most recently drawn. */
static POINT dragPoint;         /* Location of last mouse move message. */
/*
 * TemplateChildWindow
 *
 * This is the main callback routine for the window which is used to display
 * a template for retrieving intraoral images.
 */
WINDOW_PROC TemplateChildWindow(HWND wnd, WORD msg, WORD wP, LONG lP) {
    LONG retVal = NULL;
    HDC hDC;
    PAINTSTRUCT ps;
    RECT rect;
```

```c
BOOL removed;
HANDLE oldBrush;
int ellipse;
HWND imageWnd;
StudiesPtr s;
int selWindow;
BOOL manualMode;

switch (msg) {
case DPX_ChangeMode:
    /*
     * Handle the worked associated with changing modes.  If switching to
     * automatic mode (wP = TRUE), destroy the sub-window (if there is
     * one).  Then determine if this window is to be removed.  When
     * switching to manual mode, just clear the removed field.
     */
    GetClientRect(wnd, &rect);
    if (wP) {
        imageWnd = GetWindowWord(wnd, 0);
        if (imageWnd) {
            DestroyWindow(imageWnd);
            SetWindowWord(wnd, 0, 0);
            InvalidateRect(wnd, &rect, FALSE);
        } /* if */ selWindow = GetWindowWord(GetParent(wnd), 0);
        if (selWindow == GetWindowWord(wnd, GWW_ID)) {
            SetWindowWord(wnd, 0, TRUE);
            InvalidateRect(wnd, &rect, FALSE);
        } /* if */
    } else {
        SetWindowWord(wnd, 0, FALSE);
        InvalidateRect(wnd, &rect, FALSE);
    } /* if */
    break;
case DPX_ChangeImage:
    SetWindowWord(wnd, 0, wP);
    GetClientRect(wnd, &rect);
    InvalidateRect(wnd, &rect, FALSE);
    break;
case WM_DESTROY:
    /*
     * On a destroy message, if in manual mode, the sub-image should
     * be removed.
     */
    imageWnd = GetWindowWord(wnd, 0);
    if (IsWindow(imageWnd)) {
        DestroyWindow(imageWnd);
    } /* if */
    break;
case WM_SYSCOLORCHANGE:
    /*
     * On a color change, all child windows which have a non-zero value
     * in word 0 should be re-drawn, to take into account a possible
     * change in background color.
     */
    if (GetWindowWord(wnd, 0)) {
        GetClientRect(wnd, &rect);
        InvalidateRect(wnd, &rect, FALSE);
    } /* if */
case WM_PAINT:
    manualMode = SendDlgItemMessage(gPatDlg, IDC_PTD_MANUAL,
                                              BM_GETCHECK,
                                              0,
                                              0);

if (manualMode) {
        imageWnd = GetWindowWord(wnd, 0);
        removed = imageWnd != 0 && IsWindowVisible(imageWnd);
    } else {
        removed = GetWindowWord(wnd, 0);
```

```
         } /* if */
        ellipse = GetClassWord(wnd, 0);
        /*
         * Get a device context.
         */
        hDC = BeginPaint(wnd, &ps);
        /*
         * Get the correct brush with which to fill the rectangle.
         */
        if (removed)
            oldBrush = SelectObject(hDC, ghChildBrush);
        else
            oldBrush = SelectObject(hDC, GetStockObject(DKGRAY_BRUSH));
        /*
         * Fill the window (or a rounded rectangle version of it).
         */
        GetClientRect(wnd, &rect);
        RoundRect(hDC, 0,
                       0,
                       rect.right,
                       rect.bottom,
                       ellipse,
                       ellipse);
        /*
         * Clean up.
         */
        SelectObject(hDC, oldBrush);
        ReleaseDC(wnd, hDC);
        break;
    case WM_LBUTTONDOWN:
        /*
         * Check to see if the program is in automatic or manual mode.
         */
        manualMode = SendDlgItemMessage(gPatDlg, IDC_PTD_MANUAL,
                                                 BM_GETCHECK,
                                                 0,
                                                 0);

if (manualMode) {
            /*
             * Manual mode.  If this image is already in a window, bring it
             * to the front.  Otherwise, capture the mouse and begin dragging
             * an outline around.
             */
            imageWnd = GetWindowWord(wnd, 0);
            if (imageWnd) {
                if (IsWindowVisible(imageWnd)) {
                    SetFocus(imageWnd);
                } else {
                    ShowWindow(imageWnd, SW_SHOW);
                    GetClientRect(wnd, &rect);
                    InvalidateRect(wnd, &rect, FALSE);
                } /* if */
            } else {
        s = (StudiesPtr)GlobalLock(ghStudy);
        captured = TRUE;
        SetCapture(wnd);
        /*
         * Define the rectangle taking the image orientation into
         * account.
         */
        dragPoint.x = LOWORD(lP);
        dragPoint.y = HIWORD(lP);
        ClientToScreen(wnd, &dragPoint);
        dragRect.left   = dragPoint.x;
        dragRect.top    = dragPoint.y;
        if (intra_modes[s->exam_type].images[GetWindowWord(wnd, GWW_ID)
            dragRect.right  = dragRect.left + s->x_size + 1;
            dragRect.bottom = dragRect.top  + s->y_size + 1;
        } else {
            dragRect.right  = dragRect.left + s->y_size + 1;
```

```
            dragRect.bottom = dragRect.top  + s->x_size + 1;
    } /* if */
    dragRect.right  +=   2*GetSystemMetrics(SM_CXFRAME);
    dragRect.bottom +=   2*GetSystemMetrics(SM_CYFRAME)
                       + GetSystemMetrics(SM_CYCAPTION);

/*
     * Now get a device context, and draw the first rectangle.
     */
    hDC = CreateDC("DISPLAY", NULL, NULL, NULL);
    SetROP2(hDC, R2_XORPEN);
    SelectObject(hDC, GetStockObject(WHITE_PEN));
    SelectObject(hDC, GetStockObject(NULL_BRUSH));
    Rectangle(hDC, dragRect.left,
                   dragRect.top,
                   dragRect.right,
                   dragRect.bottom);
    DeleteDC(hDC);

GlobalUnlock(ghStudy);
    } /* if */
} else {
    /*
     * Automatic mode.  If this image is not already removed, send
     * a message to the template indicating the change.
     */
    if (!GetWindowWord(wnd, 0)) {
        PostMessage(gTemplateWnd, DPX_ChangeImage,
                                  GetWindowWord(wnd, GWW_ID),
                                  0);
    } /* if */
} /* if */
break;
    case WM_MOUSEMOVE:
        if (captured) {
            /*
             * Now get a device context, undraw the old rectangle and draw
             * the new rectangle.
             */
            hDC = CreateDC("DISPLAY", NULL, NULL, NULL);
            SetROP2(hDC, R2_XORPEN);
            SelectObject(hDC, GetStockObject(WHITE_PEN));
            SelectObject(hDC, GetStockObject(NULL_BRUSH));
            Rectangle(hDC, dragRect.left,
                           dragRect.top,
                           dragRect.right,
                           dragRect.bottom);

dragPoint.x = LOWORD(lP);
            dragPoint.y = HIWORD(lP);
            ClientToScreen(wnd, &dragPoint);
            dragRect.right  += (dragPoint.x-dragRect.left);
            dragRect.bottom += (dragPoint.y-dragRect.top);
            dragRect.left   = dragPoint.x;
            dragRect.top    = dragPoint.y;
            Rectangle(hDC, dragRect.left,
                           dragRect.top,
                           dragRect.right,
                           dragRect.bottom);
            DeleteDC(hDC);
        } else {
            retVal = DefWindowProc(wnd, msg, wP, lP);
        } /* if */
        break;
    case WM_LBUTTONUP:
        if (captured) {
            /*
             * First undraw the rectangle.
             */
            hDC = CreateDC("DISPLAY", NULL, NULL, NULL);
            SetROP2(hDC, R2_XORPEN);
```

```
                SelectObject(hDC, GetStockObject(WHITE_PEN));
                SelectObject(hDC, GetStockObject(NULL_BRUSH));
                Rectangle(hDC, dragRect.left,
                               dragRect.top,
                               dragRect.right,
                               dragRect.bottom);
                DeleteDC(hDC);

ReleaseCapture();
                captured = FALSE;
                /*
                 * Now create the new window for the image.  I'm not entirely
                 * sure why, but we need to subtract one extra from the vertical
                 * dimension.  Probably has something to do with the combined
                 * size of the caption and the frame.
                 */
                imageWnd = CreateWindow("manualWClass",
                                        NULL,
                                        WS_CAPTION | WS_THICKFRAME |
                                                     WS_POPUP |
                                                     WS_MINIMIZEBOX |
                                                     WS_MAXIMIZEBOX |
                                                     WS_VSCROLL |
                                                     WS_HSCROLL,
                                        0,
                                        0,
                                        0,
                                        0,
                                        wnd,
                                        NULL,
                                        gInst,
                                        NULL
                                        );
                SetWindowWord(imageWnd, 0, GetWindowWord(wnd, GWW_ID));
                SetClassWord(imageWnd, 0, GetClassWord(wnd, 2));
                SetWindowWord(wnd, 0, imageWnd);
                GetClientRect(wnd, &rect);
                InvalidateRect(wnd, &rect, FALSE);
                MoveWindow(imageWnd, dragRect.left,
                                     dragRect.top,
                                     dragRect.right-dragRect.left-1,
                                     dragRect.bottom-dragRect.top-1-1,
                                     FALSE);
                ShowWindow(imageWnd, SW_SHOW);
            } else {
                retVal = DefWindowProc(wnd, msg, wP, lP);
            } /* if */
            break;
        default:
            retVal = DefWindowProc(wnd, msg, wP, lP);
            break;
    } /* switch */ return retVal;
} /* TemplateChildWindow */
#include "windows.h"
#include "btrieve.h"
#include "wdpx.h"
#include "resource.h"
#include "wdpxdlg.h"
#pragma hdrstop
#include "tmplwnd.h"
#include "messages.h"
/*
 * ColorChangeEnum
 *
 * Local routine called by EnumChildWindows when a color change occurs.  The
 * lP field is not used.
 */
static BOOL FAR PASCAL _export ColorChangeEnum(HWND wnd, DWORD lP) {
    SendMessage(wnd, WM_SYSCOLORCHANGE, 0 ,0);
```

```
        return TRUE;
} /* ColorChangeEnum */
/*
 * ModeChangeEnum
 *
 * Local routine called by EnumChildWindows when a mode change occurs.  The
 * lP field is used to hold the new mode.
 */
static BOOL FAR PASCAL _export ModeChangeEnum(HWND wnd, DWORD lP) {
    SendMessage(wnd, DPX_ChangeMode, lP ,0);

return TRUE;
} /* ModeChangeEnum */
/*
 * CreateTemplate
 *
 * Local routine to fill the template.
 */
static void CreateTemplate(HWND wnd) {
    StudiesPtr study;
    int wheight, wwidth;
    long top, left, height, width;
    int twidth, theight;
    int images;
    ExamTypes exam_type;
    Orientations o;
    int ellipse;
    int i;
    RECT rect;
    /*
     * Get the size of the window.
     */
    GetClientRect(wnd, &rect);
    wwidth = rect.right;
    wheight = rect.bottom;

study = (StudiesPtr)GlobalLock(ghStudy);
    /*
     * Get the information to compute the scaling factor for this template.
     */
    exam_type = study->exam_type;

twidth  = intra_modes[exam_type].mmWidth;
    theight = intra_modes[exam_type].mmHeight;

images = intra_modes[exam_type].numImages;
    /*
     * Now use these values to create the sub-windows for the template.
     */
    width  = 40L * wwidth  / twidth;
    height = 30L * wheight / theight;
    ellipse =  5L * wwidth  / twidth;
    for (i = 0 ; i < images ; i += 1) {
        HWND child;
        int w,h;

left = intra_modes[exam_type].images[i].corner.x;
        top  = intra_modes[exam_type].images[i].corner.y;
        o    = intra_modes[exam_type].images[i].portrait;

left = left * wwidth  / twidth;
        top  = top  * wheight / theight;

w = (o == landscape) ? width : height;
        h = (o == landscape) ? height : width;
        child = CreateWindow("templateChildWClass",
                             NULL,
                             WS_CHILDWINDOW|WS_VISIBLE,
                             left,
                             top,
```

```
                            w,
                            h,
                            wnd,
                            i,
                            GetWindowWord(wnd, GWW_HINSTANCE),
                            NULL
                            );
        if (!child) {
            MessageBox(wnd, "Cannot create template",
                       NULL,
                       MB_OK|MB_SYSTEMMODAL|MB_ICONSTOP);
        } /* if */
        SetWindowWord(child, 0, i == 0);
    } /* for */
    /*
     * Define the ellipse value for the children.
     */
    SetClassWord(GetWindow(wnd, GW_CHILD), 0, ellipse);
    /*
     * Cleanup.
     */
    GlobalUnlock(ghStudy);
} /* CreateTemplate */
/*
 * DestroyTemplate
 *
 * Local routine to clean up the child windows.
 */
static void DestroyTemplate(HWND wnd) {
    HWND child;

while ((child = GetWindow(wnd, GW_CHILD)) != NULL) {
        DestroyWindow(child);
    } /* while */
} /* DestroyTemplate */
/*
 * SizeTemplate
 *
 * Local routine to re-size the template to fit in the space.
 */
static void SizeTemplate(HWND wnd, StudiesPtr s) {
    double screen, physical;
    int wwidth, wheight, wX, wY;
    int twidth, theight;
    ExamTypes exam_type;
    int width, height;
    int X, Y;

exam_type = s->exam_type;

wX       = GetWindowWord(wnd, 2);
    wY       = GetWindowWord(wnd, 4);
    wwidth   = GetWindowWord(wnd, 6);
    wheight  = GetWindowWord(wnd, 8);
    screen   = (double)wwidth / (double)wheight;

twidth   = intra_modes[exam_type].mmWidth;
    theight  = intra_modes[exam_type].mmHeight;
    physical = (double)twidth / (double)theight;

if (physical <= screen) {
        height = wheight;
        width  = wheight * physical;
    } else {
        width  = wwidth;
        height = width / physical;
    } /* if */

X = wX + (wwidth - width)/2;
    Y = wY + (wheight - height)/2;
```

```
    MoveWindow(wnd, X, Y, width, height, FALSE);
} /* SizeTemplate */
/*
 * TemplateWindow
 *
 * This is the main callback routine for the window which is used to display
 * a template for retrieving intraoral images.
 */
WINDOW_PROC TemplateWindow(HWND wnd, WORD msg, WORD wP, LONG lP) {
    LONG retVal = NULL;
    StudiesPtr study;
    FARPROC enumProc;

switch (msg) {
    case WM_DESTROY:
        break;
    case WM_SYSCOLORCHANGE:
        /*
         * Create a new brush the same color as the background, and invalidate
         * all the children who are affected.
         */
        DeleteObject(ghChildBrush);
        ghChildBrush = CreateSolidBrush(GetSysColor(COLOR_BACKGROUND));

enumProc = MakeProcInstance((FARPROC)ColorChangeEnum, gInst);
        EnumChildWindows(wnd, enumProc, 0);
        FreeProcInstance(enumProc);
        break;
    case DPX_ChangeStudy:
        /*
         * Here, if the current study is an intraoral, display the appropriate
         * template.
         */
        study = (StudiesPtr)GlobalLock(ghStudy);
        if (study->modality == intra_mode) {
            ShowWindow(wnd, SW_HIDE);
            DestroyTemplate(wnd);
            SizeTemplate(wnd, study);
            CreateTemplate(wnd);
            ShowWindow(wnd, SW_SHOW);
            SetWindowWord(wnd, 0, 0);
            /*
             * Keep the image handle.
             */
            SetClassWord(GetWindow(wnd, GW_CHILD), 2, wP);
        } else {
            ShowWindow(wnd, SW_HIDE);
            DestroyTemplate(wnd);
        } /* if */
        GlobalUnlock(ghStudy);
        break;
    case DPX_ClearPatient:
    case DPX_ChangePatient:
        /*
         * In either of these cases, we should hide the window and destroy
         * all the child windows.
         */
        ShowWindow(wnd, SW_HIDE);
        DestroyTemplate(wnd);
        break;
    case DPX_ChangeImage:
        /*
         * Tell the image window and the two children involved that the image
         * has changed.
         */
        PostMessage(GetDlgItem(wnd, GetWindowWord(wnd, 0)),
                    DPX_ChangeImage,
                    FALSE,
                    0);
```

```
            PostMessage(GetDlgItem(wnd, wP),
                       DPX_ChangeImage,
                       TRUE,
                       0);
            PostMessage(gImageWnd,
                       DPX_ChangeImage,
                       wP,
                       0);
            SetWindowWord(wnd, 0, wP);
            break;
        case DPX_ChangeMode:
            /*
             * Hide or show the window based upon the value of wP.  If changing
             * to automatic mode, tell each child so that they can get rid of the
             * manual image window associated.  If switching to manual mode,
             * we need only tell the selected child.
             *     wP = TRUE => switching to automatic mode.
             */
            if (wP) {
                enumProc = MakeProcInstance((FARPROC)ModeChangeEnum, gInst);
                EnumChildWindows(wnd, enumProc, wP);
                FreeProcInstance(enumProc);
                ShowWindow(gImageWnd, SW_SHOW);
            } else {
                PostMessage(GetDlgItem(wnd, GetWindowWord(wnd, 0)), DPX_ChangeMode,
                                                                    FALSE,
                                                                    0);
                ShowWindow(gImageWnd, SW_HIDE);
            } /* if */
            break;
        default:
            retVal = DefWindowProc(wnd, msg, wP, lP);
            break;
    } /* switch */ return retVal;

} /* TemplateWindow */
  /*
   *
   *   PROGRAM: wdpx.c
   *
   *   PURPOSE: This is the main source file for the Windows 3.0 version of
   *            DPX1000.
   *
   */
#define EXTERN
#pragma hdrstop
#include "windows.h"
#include "btrieve.h"
#include "wdpx.h"
#include "resource.h"
#include "wdpxdlg.h"
#include "ptd.h"
#include "mainwind.h"
#include "dbutil.h"
#include "cmntwnd.h"
#include "autownd.h"
#include "tmplwnd.h"
#include "tmplchld.h"
#include "manimage.h"
#include "acquire.h"

#include <string.h>
#include <stdio.h>
/*
 * CreateGrayPalette
 *
 * This routine creates a 240 shades of gray palette for use in displaying
 * the images.
```

```c
*/
HPALETTE CreateGrayPalette(void) {
    int i;
    LOGPALETTE *pPal;
    HANDLE hLPal;
    HPALETTE hPal;

hLPal = LocalAlloc(LMEM_ZEROINIT|LMEM_MOVEABLE,
                       sizeof(LOGPALETTE)+240*sizeof(PALETTEENTRY));
    if (!hLPal)
        return NULL;
    pPal = (LOGPALETTE *)LocalLock(hLPal);

pPal->palVersion    = 0x300;
    pPal->palNumEntries = 240;
    for (i = 0 ; i < 240 ; i += 1) {
        pPal->palPalEntry[i].peRed   =
        pPal->palPalEntry[i].peGreen =
        pPal->palPalEntry[i].peBlue  = (unsigned char)i;
        pPal->palPalEntry[i].peFlags = 0;
    } /* for */ hPal = CreatePalette(pPal);

LocalUnlock(hLPal);
    LocalFree(hLPal);

return hPal;
} /* CreateGrayPalette */
/*
 * CreateGrayDIB
 *
 * Local routine to allocate the global DIB which contains 256 shades of
 * gray.  To use this, the window must set the width and height values.
 * Also, the window must be sure not to surrender control, since other
 * windows may wish to use the DIB.
 */
static HANDLE CreateGrayDIB(void) {
    HANDLE hDib;
    LPBITMAPINFO theDib;
    int i;
    /*
     * Allocate the offscreen bitmap.
     */
    hDib = GlobalAlloc(GMEM_MOVEABLE | GMEM_ZEROINIT, sizeof(BITMAPINFOHEADER)
                                                      256*sizeof(RGBQUAD));
    if (hDib) {
        theDib = (LPBITMAPINFO)GlobalLock(hDib);
        /*
         * Fill the bitmap header.
         */
        theDib->bmiHeader.biSize          = (long)sizeof(BITMAPINFOHEADER);
        theDib->bmiHeader.biWidth         = 0;
        theDib->bmiHeader.biHeight        = 0;
        theDib->bmiHeader.biPlanes        = 1;
        theDib->bmiHeader.biBitCount      = 8;
        theDib->bmiHeader.biCompression   = BI_RGB;
        theDib->bmiHeader.biSizeImage     = 0L;
        theDib->bmiHeader.biXPelsPerMeter = 0L;
        theDib->bmiHeader.biYPelsPerMeter = 0L;
        theDib->bmiHeader.biClrUsed       = 0L;
        theDib->bmiHeader.biClrImportant  = 0L;
        /*
         * Fill the color table.
         */
        for (i = 0 ; i < 256 ; i += 1) {
            theDib->bmiColors[i].rgbRed   =
            theDib->bmiColors[i].rgbGreen =
            theDib->bmiColors[i].rgbBlue  = (BYTE)i;
        } /* for */
```

```c
        /*
         * All done with the display context.
         */
        GlobalUnlock(hDib);
    } /* if */ return hDib;
} /* CreateGrayDIB */
/*
 *  FUNCTION: InitApplication(HANDLE)
 *
 *  PURPOSE: Initializes window data and registers window class
 *
 *  COMMENTS:
 *
 *      This function is called at initialization time only if no other
 *      instances of the application are running.  This function performs
 *      initialization tasks that can be done once for any number of running
 *      instances.
 *
 *      In this case, we initialize a window class by filling out a data
 *      structure of type WNDCLASS and calling the Windows RegisterClass()
 *      function.  Since all instances of this application use the same window
 *      class, we only need to do this when the first instance is initialized.
 *
 */
#pragma warn -sus
static BOOL InitApplication(HANDLE hInstance) {
    WNDCLASS   wc;
    /*
     * Fill in window class structure with parameters that describe the
     * main window.
     */
    wc.style         = NULL;
    wc.lpfnWndProc   = MainWndProc;
    wc.cbClsExtra    = 0;
    wc.cbWndExtra    = 0;
    wc.hInstance     = hInstance;
    wc.hIcon         = LoadIcon(hInstance, "XRayIcon");
    wc.hCursor       = LoadCursor(NULL, IDC_ARROW);
    wc.hbrBackground = GetStockObject(WHITE_BRUSH);
    wc.lpszMenuName  = "wdpxMenu";
    wc.lpszClassName = "wdpxWClass";
    /*
     * Register the window class.
     */
    if (!RegisterClass(&wc))
        return FALSE;
/*
 * Fill in window class structure with parameters that describe the
 * comments window.
 */
wc.style         = NULL;
wc.lpfnWndProc   = (FARPROC)StudyComments;
wc.cbClsExtra    = 0;
wc.cbWndExtra    = 0;
wc.hInstance     = hInstance;
wc.hIcon         = NULL;
wc.hCursor       = LoadCursor(NULL, IDC_ARROW);
wc.hbrBackground = GetStockObject(WHITE_BRUSH);
wc.lpszMenuName  = NULL;
wc.lpszClassName = "commentWClass";
/*
 * Register the window class.
 */
if (!RegisterClass(&wc))
    return FALSE;
/*
 * Fill in window class structure with parameters that describe the
 * auto image window.  We keep 2 extra bytes around so that each window
 * can keep track of which image it is, and 2 bytes to hold the handle
 * to the image data.
```

```
 *
 * Extra data
 *      Class           (none)
 *      Window          0           Handle to image data.
 *                      2           Image index.
 */
wc.style          = NULL;
wc.lpfnWndProc    = (FARPROC)AutomaticWindow;
wc.cbClsExtra     = 0;
wc.cbWndExtra     = 4;
wc.hInstance      = hInstance;
wc.hIcon          = NULL;
wc.hCursor        = LoadCursor(NULL, IDC_ARROW);
wc.hbrBackground  = GetStockObject(BLACK_BRUSH);
wc.lpszMenuName   = NULL;
wc.lpszClassName  = "autoWClass";
/*
 * Register the window class.
 */
if (!RegisterClass(&wc))
    return FALSE;
/*
 * Fill in window class structure with parameters that describe the
 * template window.  We keep 2 extra bytes around so that the window
 * can keep track of which image is current, and 8 bytes to keep the
 * rectangle of the free area.
 */
wc.style          = NULL;
wc.lpfnWndProc    = (FARPROC)TemplateWindow;
wc.cbClsExtra     = 0;
wc.cbWndExtra     = 10;
wc.hInstance      = hInstance;
wc.hIcon          = NULL;
wc.hCursor        = LoadCursor(NULL, IDC_ARROW);
wc.hbrBackground  = GetStockObject(BLACK_BRUSH);
wc.lpszMenuName   = NULL;
wc.lpszClassName  = "templateWClass";
/*
 * Register the window class.
 */
if (!RegisterClass(&wc))
    return FALSE;
/*
 * Register the class that defines the child windows used in the template
 * window.
 *
 * Extra data
 *      Class           0           Ellipse value
 *                      2           Image data handle
 *      Window          0           Selected, or handle to image window.
 */
wc.style          = NULL;
wc.lpfnWndProc    = (FARPROC)TemplateChildWindow;
wc.cbClsExtra     = 4;
wc.cbWndExtra     = 2;
wc.hInstance      = hInstance;
wc.hIcon          = NULL;
wc.hCursor        = LoadCursor(NULL, IDC_ARROW);
wc.hbrBackground  = GetStockObject(BLACK_BRUSH);
wc.lpszMenuName   = NULL;
wc.lpszClassName  = "templateChildWClass";
/*
 * Register the window class.
 */
if (!RegisterClass(&wc))
    return FALSE;
/*
 * Register the class that defines the windows used in manual image
 * display mode.
 * Extra data:
```

```
 *      Class          0         Handle to image data.
 *      Window         0         Number of image.
 */
wc.style         = NULL;
wc.lpfnWndProc   = (FARPROC)ManualImageWindow;
wc.cbClsExtra    = 2;
wc.cbWndExtra    = 2;
wc.hInstance     = hInstance;
wc.hIcon         = NULL;
wc.hCursor       = LoadCursor(NULL, IDC_ARROW);
wc.hbrBackground = GetStockObject(BLACK_BRUSH);
wc.lpszMenuName  = NULL;
wc.lpszClassName = "manualWClass";
/*
 * Register the window class.
 */
if (!RegisterClass(&wc))
    return FALSE;
/*
 * Everything worked, return TRUE.
 */
return TRUE;
} /* InitApplication */
#pragma warn .sus
/*
 * FUNCTION:  InitInstance(HANDLE, int)
 *
 * PURPOSE:  Saves instance handle and creates main window
 *
 * COMMENTS:
 *
 *     This function is called at initialization time for every instance of
 *     this application.  This function performs initialization tasks that
 *     cannot be shared by multiple instances.
 *
 *     In this case, we save the instance handle in a static variable and
 *     create and display the main program window.
 *
 */
static BOOL InitInstance(HANDLE hInstance, int nCmdShow) {
    FARPROC dlgProc;
    int screenX, mainWY;
    RECT rect;
    int patRight, patBottom;
    char aString[32];
    /*
     * Save the instance handle in static variable, which will be used in
     * any subsequent calls from this application to Windows.
     */
    gInst = hInstance;
    /*
     * Initialize other global variables.
     */
    gIsAPatient = gIsAStudy = FALSE;
    ghPatient = GlobalAlloc(GMEM_MOVEABLE | GMEM_ZEROINIT,
                            sizeof(PatientRecord));
    ghStudy   = GlobalAlloc(GMEM_MOVEABLE | GMEM_ZEROINIT,
                            sizeof(StudiesRecord));
    ghDisk    = GlobalAlloc(GMEM_MOVEABLE | GMEM_ZEROINIT,
                            sizeof(DiskRecord));
    gImageWnd = 0;

gPalette = CreateGrayPalette();
    if (gPalette == NULL)
        return FALSE;

ghDIB = CreateGrayDIB();
    if (ghDIB == NULL)
        return FALSE;
    /*
```

```c
 * We need a brush which we use to paint "empty" tmeplate child windows.
 * We will use a brush the same color as the background.
 */
ghChildBrush = CreateSolidBrush(GetSysColor(COLOR_BACKGROUND));
/*
 * Get the screen sizes which we use to size the windows.
 */
screenX = GetSystemMetrics(SM_CXSCREEN);
mainWY  = GetSystemMetrics(SM_CYCAPTION) +
          GetSystemMetrics(SM_CYMENU) +
          2*GetSystemMetrics(SM_CYBORDER)-1;
/*
 * Create a main window for this application instance.
 */
gMainWindow = CreateWindow("wdpxWClass",
                          "WDPX",
                          WS_OVERLAPPED | WS_CAPTION |
                                          WS_SYSMENU |
                                          WS_MINIMIZEBOX |
                                          WS_VISIBLE,
                          0,
                          0,
                          screenX,
                          mainWY,
                          NULL,
                          NULL,
                          hInstance,
                          NULL
                          );
/*
 * If window could not be created, return "failure".
 */
if (!gMainWindow)
    return FALSE;
/*
 * Create and display the patient info dialog.
 */
dlgProc = MakeProcInstance((FARPROC)PatientDisplay, gInst);
gPatDlg = CreateDialog(gInst, "PatientDisplay", gMainWindow, dlgProc);
if (gPatDlg == NULL)
    return FALSE;
/*
 * Create the comments entry window.
 */
LoadString(gInst, IDS_CommentsTitle, aString, 31);
gCommentWnd = CreateWindow("commentWClass",
                          aString,
                          WS_OVERLAPPED | WS_MAXIMIZEBOX,
                          (screenX-200)/2,
                          mainWY+30,
                          400,
                          200,
                          gPatDlg,
                          NULL,
                          hInstance,
                          NULL
                          );
/*
 * If window could not be created, return "failure".
 */
if (!gCommentWnd)
    return FALSE;
/*
 * Create the template window, but leave it hidden.  Fill in the extra
 * words.
 */
GetWindowRect(gPatDlg, &rect);
patRight  = rect.right;
patBottom = rect.bottom;
gTemplateWnd = CreateWindow("templateWClass",
```

```c
                              NULL,
                              WS_POPUP|WS_BORDER,
                              patRight+1,
                              mainWY+1,
                              screenX-patRight-2,
                              patBottom-mainWY-2,
                              gMainWindow,
                              NULL,
                              hInstance,
                              NULL
                              );
    if (!gTemplateWnd)
        return FALSE;

SetWindowWord(gTemplateWnd, 0, 0)
    SetWindowWord(gTemplateWnd, 2, patRight+1);
    SetWindowWord(gTemplateWnd, 4, mainWY+1);
    SetWindowWord(gTemplateWnd, 6, screenX-patRight-2);
    SetWindowWord(gTemplateWnd, 8, patBottom-mainWY-2);

gResultsWnd = NULL;
    /*
     * Open the database.
     */
    OpenDB();
    /*
     * All done, everything was successful.
     */
    return TRUE;
} /* InitInstance */
/*
 * WinMain
 *
 * Calls initialization function, processes message loop.  We allow only
 * one instance of the application.
 */
int PASCAL WinMain(HANDLE instance, HANDLE prev, LPSTR cmdLine, int cmdShow) {
    MSG msg;
    char acquireString[64];
    int px,py,ix,iy;
    BOOL found;

if (prev) {
        return FALSE;
    } else {
        if (!InitApplication(instance)) {
            return FALSE;
        } /* if */
    } /* if */
    /*
     * Perform initializations that apply to a specific instance.
     */
    if (!InitInstance(instance, cmdShow))
        return FALSE;
    /*
     * Set the acquired image sizes based upon values in the win.ini file.
     */
    GetProfileString(gAppName,
                     "Acquire sizes",
                     "z",
                     acquireString,
                     64);
    if (acquireString[0] == 'z') {
        px = 1024;
        py = 512;
        ix = 384;
    iy = 576;
    found = FALSE;
} else {
    sscanf(acquireString, "%d,%d,%d,%d", &px, &py, &ix, &iy);
```

```c
            found = TRUE;
        } /* if */
    SetAcquireDim(pano_mode, px, py, FALSE);
    SetAcquireDim(intra_mode, ix, iy, !found);
    /*
     * Initially, we would like the about box displayed, so we will post a
     * fake WM_COMMAND message to the main window.
     */
    PostMessage(gMainWindow, WM_COMMAND, IDM_About, 0);
    /*
     * Acquire and dispatch messages until a WM_QUIT message is received.
     */
    while (GetMessage(&msg, NULL, NULL, NULL)) {
        if (gPatDlg == NULL || !IsDialogMessage(gPatDlg,&msg)) {
            TranslateMessage(&msg);
            DispatchMessage(&msg);
        } /* if */
    } /* while */
    /*
     * Got to close the database.
     */
    CloseDB();
    /*
     * Free up the global memory we allocated.
     */
    GlobalFree(ghPatient);
    GlobalFree(ghStudy);
    GlobalFree(ghDisk);
    /*
     * Get rid of the GDI objects we created.
     */
    DeleteObject(gPalette);
    DeleteObject(ghChildBrush);

return msg.wParam;
} /* WinMain */
    /*
     * Declaration types for callback procedures.
     */
    #define DIALOG_PROC BOOL FAR PASCAL _export
    #define WINDOW_PROC long FAR PASCAL _export
    /*
     * Data type which defines the record which is returned from any of the
     * Get...Key() routines, and an enum that lists all the key numbers.
     */
    typedef enum {
       NoKey = -1,
       IDKey = 0,
       NameKey,
       DoBKey,
       IDStudyKey = 0,
       LabelKey = 0
    } KeyNumber;

typedef struct {
       KeyNumber keyNo;          /* Number of selected key. */
       char key[256];            /* String containing key. */
       int length;               /* Number of bytes in key. */
    } KeyRecord, *KeyRecPtr;
    /*
     * Database data types.
     */
    typedef struct {
       unsigned char day;
```

```c
    unsigned char month;
    unsigned short year;
} DBDate;

typedef struct {
    unsigned char hundredths;
    unsigned char seconds;
    unsigned char minutes;
    unsigned char hours;
} DBTime;

typedef enum {
    pano_mode = 0,
    intra_mode,
    extra_mode,
    ceph_mode
} Modalities;

typedef enum {
    complete_type = 0,
    fmx20_type = 0,
    fmx14_type,
    bw4_type,
    bw2_type
} ExamTypes;
/*
 * Database record structures.
 */
#define CHART_LEN 20
#define NAME_LEN 20
#define MAX_COMMENT (2048)

typedef struct {
    char chart_number[CHART_LEN];
    short modality;
    short exam_type;
    DBDate date_of_exp;
} StudyKey, FAR *StudyKeyPtr;

typedef struct {
    char chart_number[CHART_LEN];      /* Patient's chart number. */
    char key_first_name[NAME_LEN];     /* First name in a form that allows for
                                          case-insensitive lookups. */
    char key_middle_name[NAME_LEN];    /* Middle name case-insensitive. */
    char key_last_name[NAME_LEN];      /* Last name case-insensitive. */
    DBDate date_of_birth;              /* Patient's date of birth. */
    char first_name[NAME_LEN];         /* First name as entered by user. */
    char middle_name[NAME_LEN];        /* Middle name. */
    char last_name[NAME_LEN];          /* Last name. */
} PatientRecord, FAR *PatientPtr;

typedef struct {
    char chart_number[CHART_LEN];      /* Patient's chart number. */
    short modality;                    /* Study modality. Integer from enum. */
    short exam_type;                   /* Type of exam. Integer from enum. */
    DBDate date_of_exp;                /* Date of examination. */
    DBTime time_of_exp;                /* Time of examination. */
    short x_size;                      /* X dimension of study images. */
```

```c
        short y_size;                      /* Y size of images. */
    char referring_service[NAME_LEN];      /* Name of referring service. */
    char referring_doctor[NAME_LEN];       /* Name of referring doctor. */
    char image_file[13];                   /* Image filename. */
    char disk_label[13];                   /* Label of disk in which image file is stored. */
    short status;                          /* Interpretation status. Integer from enum. */
    char comments[MAX_COMMENT];            /* Comments. Variable length. */
} StudiesRecord, FAR *StudiesPtr;

typedef struct {
    char disk_label[13];
    unsigned long last_file;
    unsigned long capacity;
    unsigned long volume;
} DiskRecord, FAR *DiskPtr;

typedef enum {
    portrait = TRUE,
    landscape = FALSE
} Orientations;

typedef struct {
    POINT corner;            /* Position of upper-left corner (in mm) */
    BOOL  portrait;          /* x-ray is oriented portrait in holder. */
} ImageInfo, NEAR *ImageInfoPtr;

typedef struct {
    char far *name;          /* Name to be displayed. */
    int numImages;           /* Number of images in study. */
    short mmWidth;           /* Width of holder in mm. */
    short mmHeight;          /* Height of holder in mm. */
    ImageInfo images[24];    /* Data for each image in holder. */
} ModelInfo, NEAR *ModelInfoPtr;

typedef enum {
    January=0, February, March, April, May, June, July,
    August, September, October, Novenber, December
} monthEnum;

typedef unsigned char far *ImagePtr;
/*
 * Global data.  Most global variable names begin with the letter 'g'.
 */
#ifndef EXTERN
define EXTERN extern EXTERN char *gAppName;

EXTERN char *month_names[12];
EXTERN char *month_abbrs[12];
EXTERN int month_days[12];

EXTERN char far *mode_strings[];

EXTERN ModelInfo pano_modes[];
EXTERN ModelInfo intra_modes[];

EXTERN char far *interp_strings[];
```

```
#else
/*
 * The application name.
 */
char *gAppName = "WDPX";
/*
 * Stuff for converting dates.
 */
char *month_names[12] = {
    "January", "February", "March", "April", "May", "June",
    "July", "August", "September", "October", "November", "December"
};
char *month_abbrs[12] = {
    "Jan", "Feb", "Mar", "Apr", "May", "Jun",
    "Jul", "Aug", "Sep", "Oct", "Nov", "Dec"
};
int month_days [12] = { 31, 28, 31, 30, 31, 30, 31, 31, 30, 31, 30, 31 };
/*
 * Strings which appear in the modality, exam type, and interpretation
 * status drop-down boxes.
 */
char far *mode_strings[] = {
    "Panoramic",
    "Intraoral",
    "Extraoral",
    "Cephalometric",
    0
};
    ModeInfo pano_modes[] = {
        { "Complete", 1, 0,   0 },
        { 0, 0, 0, 0 }
    };

ModeInfo intra_modes[] = {
        { "FMX(20)", 20, 345, 124,
            {
                { {   4, 10 }, landscape },
                { {  49, 10 }, landscape },
                { {   4, 48 }, landscape },
                { {  49, 48 }, landscape },
                { {   4, 87 }, landscape },
                { {  49, 87 }, landscape },
                { { 100, 17 }, portrait },
                { { 130, 17 }, portrait },
                { { 160, 17 }, portrait },
                { { 190, 17 }, portrait },
                { { 220, 17 }, portrait },
                { { 130, 70 }, portrait },
                { { 160, 70 }, portrait },
                { { 190, 70 }, portrait },
                { { 257, 10 }, landscape },
                { { 301, 10 }, landscape },
                { { 257, 48 }, landscape },
                { { 301, 48 }, landscape },
                { { 257, 87 }, landscape },
                { { 301, 87 }, landscape }
            }
```

```
},
{ "FMX(14)", 14, 290, 108,
    {
        { {   3, 14 }, landscape },
        { {  49, 14 }, landscape },
        { {   3, 66 }, landscape },
        { {  49, 66 }, landscape },
        { {  94,  8 }, portrait  },
        { { 130,  8 }, portrait  },
        { { 165,  8 }, portrait  },
        { {  94, 61 }, portrait  },
        { { 130, 61 }, portrait  },
        { { 165, 61 }, portrait  },
        { { 201, 14 }, landscape },
        { { 247, 14 }, landscape },
        { { 201, 66 }, landscape },
        { { 247, 66 }, landscape }
    }
},
{ "BW(4)",   4, 191, 70,
    {
        { {   8, 23 }, landscape },
        { {  52, 23 }, landscape },
        { {  98, 23 }, landscape },
        { { 142, 23 }, landscape }
    }
},
{ "BW(2)",   2, 102, 70,
    {
        { {   9, 22 }, landscape },
        { {  54, 22 }, landscape }
    }
},
{ 0, 0, 0, 0 }
};

char far *interp_strings[] = {
    "Pending",
    "Complete",
    0
};
#endif

EXTERN PatientPtr gPatient;

EXTERN HWND gInst;          /* Global copy of current instance of app. */
EXTERN KeyRecord gKey;      /* Global pointer to a key record.  Used to
                               simplify communication between database
                               dialog callback functions. */
EXTERN HWND gMainWindow;    /* Handle to the main window. */
EXTERN HWND gPatDlg;        /* Handle to the non-modal dialog which
                               displays the information about the
                               current patient and image set. */
EXTERN HWND gAcqDlg;        /* Handle to the non-modal dialog through
                               which the user controls the acquisition
                               process. */
EXTERN HWND gCommentWnd;    /* Handle to the comments entry window. */
```

```
    EXTERN HWND gTemplateWnd;       /* Handle to the template window. */
    EXTERN HWND gToolWnd;           /* Handle to the tools window. */
    EXTERN HANDLE ghPatient;        /* Global patient record used by dialog
                                       callback routines. */
    EXTERN BOOL gIsAPatient;        /* Is there a patient record in gPatient? */
    EXTERN HANDLE ghStudy;          /* Global studies record used by dialog
                                       callback routines. */
    EXTERN BOOL gIsAStudy;          /* Is there a study record in gStudy? */
    EXTERN HANDLE ghDisk;           /* Global disks database record. */
    EXTERN char gOpenName[132];     /* Global filename buffer.  The result of
                                       calling the GetFile dialog is placed in
                                       this buffer. */
    EXTERN char gPatPB[128];        /* Patient file position block. */
    EXTERN char gStudyPB[128];      /* Study file position block. */
    EXTERN char gDiskPB[128];       /* Disk file position block. */

EXTERN HWND gImageWnd;          /* Handle to the currently active image
                                       window. */
    EXTERN HWND gResultsWnd;        /* Handle to the results window. */
    EXTERN HANDLE ghDIB;            /* Handle to a 256-gray DIB. */
    EXTERN HBRUSH ghChildBrush;     /* Handle to the brush used to paint the
                                       template child windows. */
    EXTERN HPALETTE gPalette;       /* Handle to palette containing gray levels. */
    EXTERN BOOL gAcquiring;         /* Is the system in acquisition mode? */
/*
 *
 * PROGRAM: wdpx.c
 *
 * PURPOSE: This is the main source file for the Windows 3.0 version of
 *          DPX1000.
 *
 */
#define EXTERN
#pragma hdrstop
#include "windows.h"
#include "btrieve.h"
#include "wdpx.h"
#include "resource.h"
#include "wdpxdlg.h"
#include "ptd.h"
#include "mainwind.h"
#include "dbutil.h"
#include "cmntwnd.h"
#include "autownd.h"
#include "tmplwnd.h"
#include "tmplchld.h"
#include "manwnd.h"
#include "acquire.h"
#include "acqcntl.h"
#include "wndwords.h"
#include "toolwnd.h"

#include <string.h>
#include <stdio.h>
/*
 * CreateGrayPalette
 *
```

* This routine creates a 240 shades of gray palette for use in displaying
 * the images.
 */
```
HPALETTE CreateGrayPalette(void) {
   int i;
   LOGPALETTE *pPal;
   HANDLE hLPal;
   HPALETTE hPal;

hLPal = LocalAlloc(LMEM_ZEROINIT|LMEM_MOVEABLE,
              sizeof(LOGPALETTE)+240*sizeof(PALETTEENTRY));
   if (!hLPal)
      return NULL;
   pPal = (LOGPALETTE *)LocalLock(hLPal);

pPal->palVersion    = 0x300;
   pPal->palNumEntries = 240;
   for (i = 0 ; i < 240 ; i += 1) {
      pPal->palPalEntry[i].peRed   =
      pPal->palPalEntry[i].peGreen =
       pPal->palPalEntry[i].peBlue = (unsigned char)i;
      pPal->palPalEntry[i].peFlags = 0;
   } /* for */ hPal = CreatePalette(pPal);

LocalUnlock(hLPal);
   LocalFree(hLPal);

return hPal;
} /* CreateGrayPalette */
/*
 * CreateGrayDIB
 *
 * Local routine to allocate the global DIB which contains 256 shades of
 * gray.  To use this, the window must set the width and height values.
 * Also, the window must be sure not to surrender control, since other
 * windows may wish to use the DIB.
 */
static HANDLE CreateGrayDIB(void) {
   HANDLE hDib;
   LPBITMAPINFO theDib;
   int i;
   /*
    * Allocate the offscreen bitmap.
    */
   hDib = GlobalAlloc(GMEM_MOVEABLE | GMEM_ZEROINIT,
sizeof(BITMAPINFOHEADER) +
                          256*sizeof(RGBQUAD));
   if (hDib) {
      theDib = (LPBITMAPINFO)GlobalLock(hDib);
      /*
       * Fill the bitmap header.
       */
   theDib->bmiHeader.biSize    = (long)sizeof(BITMAPINFOHEADER);
   theDib->bmiHeader.biWidth   = 0;
   theDib->bmiHeader.biHeight  = 0;
```

```
        theDib->bmiHeader.biPlanes        = 1;
        theDib->bmiHeader.biBitCount      = 8;
        theDib->bmiHeader.biCompression   = BI_RGB;
        theDib->bmiHeader.biSizeImage     = 0L;
        theDib->bmiHeader.biXPelsPerMeter = 0L;
        theDib->bmiHeader.biYPelsPerMeter = 0L;
        theDib->bmiHeader.biClrUsed       = 0L;
         theDib->bmiHeader.biClrImportant  = 0L;
        /*
         * Fill the color table.
         */
        for (i = 0 ; i < 256 ; i += 1) {
           theDib->bmiColors[i].rgbRed   =
           theDib->bmiColors[i].rgbGreen =
           theDib->bmiColors[i].rgbBlue  = (BYTE)i;
        } /* for */
        /*
         * All done with the display context.
         */
        GlobalUnlock(hDib);
     } /* if */ return hDib;
} /* CreateGrayDIB */
/*
 * FUNCTION: InitApplication(HANDLE)
 *
 * PURPOSE: Initializes window data and registers window class
 *
 * COMMENTS:
 *
 *      This function is called at initialization time only if no other
 *      instances of the application are running.  This function performs
 *      initialization tasks that can be done once for any number of running
 *      instances.
 *
 *      In this case, we initialize a window class by filling out a data
 *      structure of type WNDCLASS and calling the Windows RegisterClass()
 *      function.  Since all instances of this application use the same window
 *      class, we only need to do this when the first instance is initialized.
 *
 */
#pragma warn -sus
static BOOL InitApplication(HANDLE hInstance) {
   WNDCLASS wc;
   /*
    * Fill in window class structure with parameters that describe the
    * main window.
    */
   wc.style         = NULL;
   wc.lpfnWndProc   = MainWndProc;
   wc.cbClsExtra    = 0;
   wc.cbWndExtra    = 0;
   wc.hInstance     = hInstance;
   wc.hIcon         = LoadIcon(hInstance, "XRayIcon");
   wc.hCursor       = LoadCursor(NULL, IDC_ARROW);
   wc.hbrBackground = GetStockObject(WHITE_BRUSH);
```

```
wc.lpszMenuName = "wdpxMenu";
wc.lpszClassName = "wdpxWClass";
/*
 * Register the window class.
 */
if (!RegisterClass(&wc))
    return FALSE;
/*
 * Fill in window class structure with parameters that describe the
 * comments window.
 */
wc.style        = NULL;
wc.lpfnWndProc  = (FARPROC)StudyComments;
wc.cbClsExtra   = 0;
wc.cbWndExtra   = 0;
wc.hInstance    = hInstance;
wc.hIcon        = NULL;
wc.hCursor      = LoadCursor(NULL, IDC_ARROW);
wc.hbrBackground = GetStockObject(WHITE_BRUSH);
wc.lpszMenuName = NULL;
wc.lpszClassName = "commentWClass";
/*
 * Register the window class.
 */
if (!RegisterClass(&wc))
    return FALSE;
/*
 * Fill in window class structure with parameters that describe the
 * auto image window.  We keep 2 extra bytes around so that each window
 * can keep track of which image it is, and 2 bytes to hold the handle
 * to the image data.
 *
 * Extra data
 *    Class    0    Handle to image data.
 *    Window   0    Image index.
 */
wc.style        = NULL;
wc.lpfnWndProc  = (FARPROC)AutomaticWindow;
wc.cbClsExtra   = 2;
wc.cbWndExtra   = 2;
wc.hInstance    = hInstance;
wc.hIcon        = NULL;
wc.hCursor      = LoadCursor(NULL, IDC_ARROW);
wc.hbrBackground = GetStockObject(BLACK_BRUSH);
wc.lpszMenuName = NULL;
wc.lpszClassName = "autoWClass";
/*
 * Register the window class.
 */
if (!RegisterClass(&wc))
    return FALSE;
/*
 * Fill in window class structure with parameters that describe the
 * template window.
 *
 * Extra data
 *    Class       (none)
```

```
 *   Window      0      Image data.
 *               2      Free area left.
 *               4      Free area top.
 *               6      Free area right.
 *               8      Free area bottom.
 */
wc.style        = NULL;
wc.lpfnWndProc  = (FARPROC)TemplateWindow;
wc.cbClsExtra   = 0;
wc.cbWndExtra   = 10;
wc.hInstance    = hInstance;
wc.hIcon        = NULL;
wc.hCursor      = LoadCursor(NULL, IDC_ARROW);
wc.hbrBackground = GetStockObject(BLACK_BRUSH);
wc.lpszMenuName = NULL;
wc.lpszClassName = "templateWClass";
/*
 * Register the window class.
 */
if (!RegisterClass(&wc))
  return FALSE;
/*
 * Register the class that defines the child windows used in the
 * template window.
 *
 * Extra data
 *   Class       0      Ellipse value
 *               2      Image data handle
 *               4      Message that caused the creation of the
 *                      window.
 *   Window      0      Selected, or handle to image window, for
 *                      display; filled for acquire.
 */
wc.style        = NULL;
wc.lpfnWndProc  = (FARPROC)TemplateChildWindow;
wc.cbClsExtra   = 6;
wc.cbWndExtra   = 2;
wc.hInstance    = hInstance;
wc.hIcon        = NULL;
wc.hCursor      = LoadCursor(NULL, IDC_ARROW);
wc.hbrBackground = GetStockObject(BLACK_BRUSH);
wc.lpszMenuName = NULL;
wc.lpszClassName = "templateChildWClass";
/*
 * Register the window class.
 */
if (!RegisterClass(&wc))
  return FALSE;
/*
 * Register the class that defines the windows used in manual image
 * display mode.
 * Extra data:
 *   Class       0      Handle to image data.
 *   Window      0      Number of image.
 */
wc.style        = NULL;
wc.lpfnWndProc  = (FARPROC)ManualImageWindow;
```

```
  wc.cbClsExtra   = 2;
  wc.cbWndExtra   = 2;
  wc.hInstance    = hInstance;
  wc.hIcon        = NULL;
  wc.hCursor      = LoadCursor(NULL, IDC_ARROW);
  wc.hbrBackground = GetStockObject(BLACK_BRUSH);
  wc.lpszMenuName = NULL;
  wc.lpszClassName = "manualWClass";
  /*
   * Register the window class.
   */
  if (!RegisterClass(&wc))
    return FALSE;
  /*
   * Register the tool window class.
   */
  if (!RegisterToolWindow(hInstance))
    return FALSE;
  /*
   * Everything worked, return TRUE.
   */
  return TRUE;
} /* InitApplication */
#pragma warn .sus
/*
 * FUNCTION: InitInstance(HANDLE, int)
 *
 * PURPOSE: Saves instance handle and creates main window
 *
 * COMMENTS:
 *
 *      This function is called at initialization time for every instance of
 *      this application.  This function performs initialization tasks that
 *      cannot be shared by multiple instances.
 *
 *      In this case, we save the instance handle in a static variable and
 *      create and display the main program window.
 *
 */
static BOOL InitInstance(HANDLE hInstance, int nCmdShow) {
FARPROC dlgProc;
 int screenX, mainWY;
RECT rect;
 int patRight, patBottom;
 char aString[32];
POINT where;
 /*
  * Save the instance handle in static variable, which will be used in
  * any subsequent calls from this application to Windows.
  */
 gInst = hInstance;
 /*
  * Initialize other global variables.
  */
 gIsAPatient = gIsAStudy = FALSE;
ghPatient = GlobalAlloc(GMEM_MOVEABLE | GMEM_ZEROINIT,
              sizeof(PatientRecord));
```

```
ghStudy  = GlobalAlloc(GMEM_MOVEABLE | GMEM_ZEROINIT,
              sizeof(StudiesRecord));
ghDisk   = GlobalAlloc(GMEM_MOVEABLE | GMEM_ZEROINIT,
              sizeof(DiskRecord));
 if (!(ghPatient && ghStudy && ghDisk)) return FALSE;
gImageWnd = 0;

gPalette  = CreateGrayPalette();
 if (gPalette == NULL)
    return FALSE;

ghDIB = CreateGrayDIB();
if (ghDIB == NULL)
    return FALSE;
/*
 * We need a brush which we use to paint "empty" tmeplate child windows.
 * We will use a brush the same color as the background.
 */
ghChildBrush = CreateSolidBrush(GetSysColor(COLOR_BACKGROUND));
/*
 * Get the screen sizes which we use to size the windows.
 */
screenX = GetSystemMetrics(SM_CXSCREEN);
mainWY  = GetSystemMetrics(SM_CYCAPTION) +
        GetSystemMetrics(SM_CYMENU) +
        2*GetSystemMetrics(SM_CYBORDER)-1;
/*
 * Create a main window for this application instance.
 */
 gMainWindow = CreateWindow("wdpxWClass",
              "WDPX",
              WS_OVERLAPPED | WS_CAPTION |
                  WS_SYSMENU |
                  WS_MINIMIZEBOX |
                  WS_VISIBLE,
             0,
             0,
             screenX,
             mainWY,
             NULL,
             NULL,
              hInstance,
             NULL
             );
/*
 * If window could not be created, return "failure".
 */
if (!gMainWindow)
    return FALSE;
/*
 * Create and display the patient info dialog.
 */
 dlgProc = MakeProcInstance((FARPROC)PatientDisplay, gInst);
  gPatDlg = CreateDialog(gInst, "PatientDisplay", gMainWindow, dlgProc);
 if (gPatDlg == NULL)
    return FALSE;
/*
```

```
 * Create the hidden acquisition control dialog.
 */
dlgProc = MakeProcInstance((FARPROC)AcquireControl, gInst);
gAcqDlg = CreateDialog(gInst, "AcquireControl", gMainWindow, dlgProc);
if (gAcqDlg == NULL)
    return FALSE;
/*
 * Create the comments entry window.
 */
 LoadString(gInst, IDS_CommentsTitle, aString, 31);
gCommentWnd = CreateWindow("commentWClass",
                aString,
               WS_OVERLAPPED | WS_MAXIMIZEBOX,
                  (screenX-200)/2,
                 mainWY+30,
                 400,
                 200,
                 gPatDlg,
                 NULL,
                  hInstance,
                 NULL
                 );
/*
 * If window could not be created, return "failure".
 */
if (!gCommentWnd)
    return FALSE;
/*
 * Create the template window, but leave it hidden.  Fill in the extra
 * words.
 */
GetWindowRect(gPatDlg, &rect);
patRight  = rect.right;
patBottom = rect.bottom;
gTemplateWnd = CreateWindow("templateWClass",
                NULL,
               WS_POPUP|WS_BORDER,
                  patRight+1,
                  mainWY+1,
                    screenX-patRight-2,
                    patBottom-mainWY-2,
                  gMainWindow,
                 NULL,
                  hInstance,
                 NULL
                 );
if (!gTemplateWnd)
    return FALSE;
/*
 * Create the tool window.
 */
where.x = GetSystemMetrics(SM_CXSCREEN) - 200;
where.y = GetSystemMetrics(SM_CYSCREEN) / 2;
 gToolWnd = CreateToolWindow(hInstance, "Tools", &where);
SetWindowWord(gTemplateWnd, TMPL_W_ImageNumber, 0);
SetWindowWord(gTemplateWnd, TMPL_W_FreeLeft,    patRight+1);
SetWindowWord(gTemplateWnd, TMPL_W_FreeTop,     mainWY+1);
```

```
      SetWindowWord(gTemplateWnd, TMPL_W_FreeWidth,   screenX-patRight-2);
      SetWindowWord(gTemplateWnd, TMPL_W_FreeHeight,  patBottom-mainWY-2);

gResultsWnd = NULL;
    /*
     * Open the database.
     */
   OpenDB();
    /*
     * All done, everything was successful.
     */
   return TRUE;
} /* InitInstance */
/*
 * WinMain
 *
 * Calls initialization function, processes message loop.  We allow only
 * one instance of the application.
 */
int PASCAL WinMain(HANDLE instance, HANDLE prev, LPSTR cmdLine, int cmdShow)
{
   MSG msg;
     char acquireString[64];
     int px,py,ix,iy;
   BOOL found;

if (prev) {
      return FALSE;
   } else {
        if (!InitApplication(instance)) {
         return FALSE;
      } /* if */
   } /* if */
   /*
     * Perform initializations that apply to a specific instance.
     */
    if (!InitInstance(instance, cmdShow))
       return FALSE;
    /*
     * Set the acquired image sizes based upon values in the win.ini file.
     */
GetProfileString(gAppName,
          "Acquire sizes",
         "z",
            acquireString,
          64);
if (acquireString[0] == 'z') {
   px = 1024;
   py = 512;
   ix = 384;
   iy = 576;
   found = FALSE;
} else {
     sscanf(acquireString, "%d,%d,%d,%d", &px, &py, &ix, &iy);
   found = TRUE;
} /* if */
SetAcquireDim(pano_mode, px, py, FALSE);
```

```
        SetAcquireDim(intra_mode, ix, iy, !found);

gAcquiring = FALSE;
    /*
     * Initially, we would like the about box displayed, so we will post a
     * fake WM_COMMAND message to the main window.
     */
    PostMessage(gMainWindow, WM_COMMAND, IDM_About, 0);
    /*
     * Acquire and dispatch messages until a WM_QUIT message is received.
     */
    while (GetMessage(&msg, NULL, NULL, NULL)) {
        if (!IsDialogMessage(gPatDlg, &msg) &&
            !IsDialogMessage(gAcqDlg, &msg)) {
            TranslateMessage(&msg);
            DispatchMessage(&msg);
        } /* if */
    } /* while */
    /*
     * Got to close the database.
     */
    CloseDB();
    /*
     * Free up the global memory we allocated.
     */
    GlobalFree(ghPatient);
    GlobalFree(ghStudy);
    GlobalFree(ghDisk);
    /*
     * Get rid of the GDI objects we created.
     */
    DeleteObject(gPalette);
    DeleteObject(ghChildBrush);

return msg.wParam;
} /* WinMain */
#ifndef TOOLWND_H
#define TOOLWND_H
/*
 * The only way to talk about tools is by the handle that this window assigns
 * them.
 */
typedef short HTOOL;
/*
 * Message sent to add a tool to the tool window.
 *
 * wP     HICON for icon which should be displayed.
 * lP     FAR pointer to Tool Proc.
 *
 * Return value
 *        HANDLE for added tool.
 */
#define TM_AddTool      (WM_USER + 0)
/*
 * Message sent to remove a single tool from the window.
 *
 * wP     HTOOL of tool to remove.
```

```
 * lP      (unused)
 *
 * Return value
 *      TRUE if tool was present.
 */
#define TM_RemoveTool   (WM_USER + 1)
/*
 * Message sent to clear all tools from window.
 *
 * wP      (unused)
 * lP      (unused)
 *
 * Return value
 *      none.
 */
#define TM_ClearTools   (WM_USER + 2)

LONG FAR PASCAL _export ToolWindowProc(HWND, WORD, WORD, LONG);
BOOL RegisterToolWindow(HWND);
HWND CreateToolWindow(HWND, LPSTR, LPPOINT);
/*
 * Tool procedures are really simple beasts, they take no parameters and
 * return no values.
 */
typedef void (FAR PASCAL *ToolProc)(void);

#endif
/*
 * ToolWnd.c
 *
 * This file contains the callback routine for the tool window class. Each
 * window requires extra space as follows:
 *
 * Class data
 *
 * Window data
 *    0    2 bytes   Handle to array of tool records.
 *    2    2 bytes   Number of slots in the array.
 *
 * Change log
 *      04/29/90 - CDW - Created original version.
 */
#include <windows.h>
#include "toolwnd.h"
/*
 * Structure containing information about tools.
 */
typedef struct {
    HICON theIcon;        /* The icon which is displayed for this tool. */
    long theProcedure;    /* The procedure which performs the work. */
} ToolRecord, FAR *LPToolRec;
/*
 * ReAllocTools
 *
 * Local routine to allocate a new buffer for the tool records and copy
 * the old tools into the new.
 */
```

```
static HANDLE ReAllocTools(HANDLE hOld, int nOld, int nNew) {
    HANDLE hNew;
    LPToolRec pOld, pNew;
    int i;

hNew = GlobalAlloc(GMEM_MOVEABLE, nNew*sizeof(ToolRecord));
    pOld = (LPToolRec)GlobalLock(hOld);
    pNew = (LPToolRec)GlobalLock(hNew);

for (i = 0 ; i < min(nOld, nNew) ; i += 1) {
        pNew[i] = pOld[i];
    } /* for */
    GlobalUnlock(hOld);
    GlobalUnlock(hNew);
    GlobalFree(hOld);

return hNew;
} /* ReAllocTools */
/*
 * SizeTheWindow
 *
 * Local routine to size the window to the correct size for the given number
 * of icons.
 */
static void SizeTheWindow(HWND wnd, int n) {
    int xIcon, yIcon, xBorder, yBorder, yCaption;
    RECT rect;
    int rows;
    int width, height;

GetWindowRect(wnd, &rect);

xIcon    = GetSystemMetrics(SM_CXICON);
    yIcon    = GetSystemMetrics(SM_CYICON);
    xBorder  = GetSystemMetrics(SM_CXBORDER);
    yBorder  = GetSystemMetrics(SM_CYBORDER);
    yCaption = GetSystemMetrics(SM_CYCAPTION);

rows   = (n+1)/2;
    width  = 2*xIcon           // 2 icons per row.
           + 1                 // vertical line dividing icons.
           + 2*xBorder;        // outline of window.
    height = yCaption          // caption and top of window.
           + yBorder           // bottom border of window.
           + rows*(yIcon+1)    // each row of icons + horizontal divider
           - 1;                // one less divider.
    MoveWindow(wnd, rect.left, rect.top,
               width, height,
               FALSE);
} /* SizeTheWindow */
/*
 * ToolWndProc
 *
 * This is the callback routine for the tools window.
 */
LONG FAR PASCAL _export ToolWndProc(HWND wnd, WORD msg, WORD wP, LONG lP)
{
```

```
LONG retVal = NULL;
HANDLE hTools;
LPToolRec pTools;
int nTools, i;
HTOOL hTool;
PAINTSTRUCT ps;
HDC hDC;
int xIcon, yIcon;
int atX, atY;
LPPOINT rgpt;
RECT rect;

switch (msg) {
case WM_NCCREATE:
    if (DefWindowProc(wnd, msg, wP, lP)) {
       hTools = GlobalAlloc(GMEM_MOVEABLE, 0);
        SetWindowWord(wnd, 0, hTools);
        SetWindowWord(wnd, 2, 0);
        retVal = hTools;
    } /* if */
    break;
case WM_CREATE:
    SizeTheWindow(wnd, 0);
    break;
case WM_DESTROY:
    GlobalFree((HANDLE)GetWindowWord(wnd, 0));
    break;
case WM_GETMINMAXINFO:
    /*
     * We need to set the minimum width lower than the default.
     */
    rgpt = (LPPOINT)lP;
    rgpt[3].x = rgpt[3].y = 0;
    break;
case WM_LBUTTONDOWN:
    /*
     * Extract the coordinates of the hit from the message.
     */
    atX = LOWORD(lP);
    atY = HIWORD(lP);
    /*
     * Get icon sizes.
     */
    xIcon = GetSystemMetrics(SM_CXICON);
    yIcon = GetSystemMetrics(SM_CYICON);
    /*
     * Convert the coordinate into the row and column numbers, and from
     * there into a tool number.
     */
    atX /= (xIcon+1);
    atY /= (yIcon+1);

hTool = atY*2 + atX;
    /*
     * Convert tool number into rectangle.
     */
    SetRect(&rect, atX*(xIcon+1),       atY*(yIcon+1),
               atX*(xIcon+1)+xIcon, atY*(yIcon+1)+yIcon);
```

```
/*
 * Get a display context and invert the rectangle.
 */
hDC = GetDC(wnd);
  InvertRect(hDC, &rect);
/*
 * Call the tool proc.
 */
  hTools = GetWindowWord(wnd, 0);
  pTools = (LPToolRec)GlobalLock(hTools);

if (pTools[hTool].theProcedure) {
      ((ToolProc)(pTools[hTool]).theProcedure)();
  } /* if */
  GlobalUnlock(hTools);
/*
 * Invert the rectangle and free up the display context.
 */
  InvertRect(hDC, &rect);
  ReleaseDC(wnd, hDC);

break;
case WM_PAINT:
   xIcon = GetSystemMetrics(SM_CXICON);
   yIcon = GetSystemMetrics(SM_CYICON);

hTools = GetWindowWord(wnd, 0);
   pTools = (LPToolRec)GlobalLock(hTools);
   nTools = GetWindowWord(wnd, 2);

hDC = BeginPaint(wnd, &ps);

atX = 0;
  atY = 0;

for (i = 0 ; i < nTools ; i += 1) {
      /*
       * Plot the icon if one is assigned to this slot.
       */
      if (pTools[i].theIcon) {
         DrawIcon(hDC, atX, atY, pTools[i].theIcon);
      } /* if */
      /*
       * Move to draw next icon.
       */
      if (i & 1) {
         /*
          * Just drew right side.  Move down and draw dividing line.
          */
         atX -= (xIcon+1);
         atY += (yIcon+1);
         MoveTo(hDC, 0, atY-1);
         LineTo(hDC, xIcon+1+xIcon, atY-1);
      } else {
         /*
          * Just drew left side. Draw vertical divider.
          */
         atX += (xIcon+1);
```

```c
            MoveTo(hDC, atX-1, atY);
            LineTo(hDC, atX-1, atY+yIcon);
        } /* if */
    } /* for */

GlobalUnlock(hTools);

EndPaint(wnd, &ps);
    break;
case TM_AddTool:
    hTool = NULL;
    /*
     * When adding a tool, we need to first scan the array to see if there
     * is an empty slot we can use.
     */
    hTools = GetWindowWord(wnd, 0);
    pTools = (LPToolRec)GlobalLock(hTools);
    nTools = GetWindowWord(wnd, 2);
    for (i = 0 ; i < nTools ; i += 1) {
        if (pTools[i].theIcon == NULL) {
            hTool = i+1;
            break;
        } /* if */
    } /* for */
    GlobalUnlock(hTools);
    /*
     * If no empty slot was found, hTool will be NULL.
     */
    if (hTool == NULL) {
        /*
         * Re-allocate the array to hold an extra item.
         */
        nTools += 1;
        hTools = ReAllocTools(hTools, nTools-1, nTools);
        /*
         * If the re-allocation was successful, place the data into the
         * new slot and resize the window if necessary.
         */
        if (hTools) {
            SetWindowWord(wnd, 0, hTools);
            SetWindowWord(wnd, 2, nTools);

if (nTools &1) {
                SizeTheWindow(wnd, nTools);
            } /* if */ hTool = nTools;
        } /* if */
    } /* if */
    /*
     * If everything has gone as expected, hTool will be non-null.
     */
    if (hTool) {
        pTools = (LPToolRec)GlobalLock(hTools);
        pTools[hTool-1].theIcon     = wP;
        pTools[hTool-1].theProcedure = lP;
        GlobalUnlock(hTools);
```

```
        } /* if */ retVal = hTool;
    break;
case TM_RemoveTool:
    /*
     * Good little programmers always check their input data.
     */
    hTools = GetWindowWord(wnd, 0);
    nTools = GetWindowWord(wnd, 2);
    if (wP > 0 && wP <= nTools) {
        pTools = (LPToolRec)GlobalLock(hTools);
        /*
         * Remove the tool from the list.
         */
        pTools[wP-1].theIcon      = 0;
        pTools[wP-1].theProcedure = 0;
        /*
         * Now, if this is the end tool, resize the window and array.
         */
        if (wP == nTools) {
            for (i = nTools-1 ; i >= 0 ; i -= 1) {
                if (pTools[i].theIcon)
                    break;
            } /* for */
        } /* if */

GlobalUnlock(hTools);
        /*
         * i is now the number of tools remaining.
         */
        if (i < nTools - 1) {
            hTools = ReAllocTools(hTools, nTools, i+1);
            nTools = i + 1;

SetWindowWord(wnd, 0, hTools);
            SetWindowWord(wnd, 2, nTools);
            SizeTheWindow(wnd, nTools);
        } /* if */
            retVal = TRUE;
        } else {
            retVal = FALSE;
        } /* if */
        break;
    case TM_ClearTools:
        hTools = GetWindowWord(wnd, 0);

hTools = ReAllocTools(hTools, GetWindowWord(wnd, 2), 0);
        SetWindowWord(wnd, 0, hTools);
        SetWindowWord(wnd, 2, 0);

SizeTheWindow(wnd, 0);
      break;
    default:
        retVal = DefWindowProc(wnd, msg, wP, lP);
      break;
    } /* switch */
```

```
        return retVal;
} /* ToolWndProc */
/*
 * RegisterToolWindow
 *
 * This routine can be called to register the Tool Window class.
 */
#pragma warn -sus
BOOL RegisterToolWindow(HWND hInstance) {
    WNDCLASS wc;

wc.style        = NULL;
    wc.lpfnWndProc  = ToolWndProc;
    wc.cbClsExtra   = 0;
    wc.cbWndExtra   = 4;
    wc.hInstance    = hInstance;
    wc.hIcon        = NULL;
    wc.hCursor      = LoadCursor(NULL, IDC_ARROW);
    wc.hbrBackground = GetStockObject(WHITE_BRUSH);
    wc.lpszMenuName = NULL;
    wc.lpszClassName = "ToolWindowClass";

return RegisterClass(&wc);
} /* RegisterToolWindow */
#pragma warn .sus
/*
 * CreateToolWindow
 *
 * This routine can be used to create a window of the tool window class.
 */
HWND CreateToolWindow(HWND hInstance, LPSTR title, LPPOINT where) {
    HWND theWindow;

theWindow = CreateWindow("ToolWindowClass",
              title,
              WS_OVERLAPPED | WS_CAPTION,
                where->x,
                where->y,
                0,
                0,
                NULL,
                NULL,
                hInstance,
                NULL
                );

return theWindow;
} /* CreateToolWindow */

HANDLE FAR FlipHorizontal(HWND, LPRECT, HANDLE);
HANDLE FAR FlipVertical(HWND, LPRECT, HANDLE);

HANDLE FAR Rotate90(HWND, LPRECT, HANDLE);
HANDLE FAR Rotate180(HWND, LPRECT, HANDLE);
HANDLE FAR Rotate270(HWND, LPRECT, HANDLE);
```

```c
/*
 * Tools.c
 *
 * This file contains the routines which implement the various image
 * processing tools.
 *
 * Change log
 *      04/30/91 - CDW - Created original version.
 */
#include <windows.h>
#include "tools.h"
#include "utils.h"

extern HPALETTE gPalette;
extern HANDLE ghDIB;
/*
 * StartBlockDisplay
 * DisplayALine
 * EndBlockDisplay
 *
 * These routines are used to isolate from the tools the buffering of display
 * lines to speed up incremental display.  All the tools need to do is call
 * StartBlockDisplay before beginning work, call DisplayALine for every
 * processed line, and EndBlockDisplay when finished.
 */
static char huge *BLOCK_data;
static int BLOCK_count;
static int BLOCK_left;
static int BLOCK_top;
static int BLOCK_width;
define LINESINABLOCK 16 static void StartBlockDisplay(LPRECT bound, int width) {
    BLOCK_left = bound->left;
    BLOCK_top  = bound->top;

BLOCK_width = width;

BLOCK_data = NULL;
} /* StartBlockDisplay */ static void DisplayALine(HDC hDC, char huge *data) {
    LPBITMAPINFO theDib;
    if (BLOCK_data == NULL) {
      BLOCK_data = data;
      BLOCK_count = 0;
    } /* if */

BLOCK_data = data;

BLOCK_count += 1;
    if (BLOCK_count == LINESINABLOCK) {
        theDib = (LPBITMAPINFO)GlobalLock(ghDIB);
        theDib->bmiHeader.biWidth = BLOCK_width;
        theDib->bmiHeader.biHeight = BLOCK_count;
```

```
        StretchDIBits(hDC,
                BLOCK_left,
                BLOCK_top,
                BLOCK_width,
                BLOCK_count,
                0,
                0,
                BLOCK_width,
                BLOCK_count,
                (LPSTR)BLOCK_data,
                theDib,
                DIB_RGB_COLORS,
                SRCCOPY);

GlobalUnlock(ghDIB);

-   BLOCK_data = NULL;
    BLOCK_top += LINESINABLOCK;
    } /* if */
} /* DisplayALine */ static void EndBlockDisplay(HDC hDC) {
    LPBITMAPINFO theDib;

if (BLOCK_data != NULL) {
        theDib = (LPBITMAPINFO)GlobalLock(ghDIB);
        theDib->bmiHeader.biWidth  = BLOCK_width;
        theDib->bmiHeader.biHeight = BLOCK_count;

StretchDIBits(hDC,
                BLOCK_left,
                BLOCK_top,
                BLOCK_width,
                BLOCK_count,
                0,
                0,
                BLOCK_width,
                BLOCK_count,
                (LPSTR)BLOCK_data,
                theDib,
                DIB_RGB_COLORS,
                SRCCOPY);

GlobalUnlock(ghDIB);
    } /* if */
} /* EndBlockDisplay */
/*
 * FlipHorizontal
 *
 * This routine rotates the image about its x-axis.
 */
HANDLE FAR FlipHorizontal(HWND wnd, LPRECT where, HANDLE oldData) {
    char huge *oldP, huge *newP;
    int y;
    HDC hDC;
    int width, height;
    long size;
    HANDLE newData;
    HCURSOR oldCursor;
```

```c
    oldCursor = SetCursor(LoadCursor(NULL, IDC_WAIT));
    /*
     * First, create a display context and select the gray palette into it.
     */
    hDC = GetDC(wnd);
    SelectPalette(hDC, gPalette, 0);
    RealizePalette(hDC);
    /*
     * Now set the dimensions of the image using the rectangle.
     */
    width  = where->right - where->left;
    height = where->bottom - where->top;
    /*
     * We will need a new buffer to hold the image while we rotate it.
     */
    size = (long)width * (long)height;
    newData = GlobalAlloc(GMEM_MOVEABLE, size);
    if (newData == NULL) return NULL;
    /*
     * Lock both the data handles.
     */
    oldP = GlobalLock(oldData);
    newP = GlobalLock(newData);
    /*
     * Now do one row at a time, plotting the pixels as they are rotated.
     * The rotation can be accomplished by moving rows from the beginning
     * of the old image to the end of the new.
     */
    newP += size-width;
    StartBlockDisplay(where, width);

for (y = 0 ; y < height ; y += 1) {
        _hmemcpy(newP, oldP, width);
        DisplayALine(hDC, newP);
        newP -= width;
        oldP += width;
    } /* for */
    EndBlockDisplay(hDC);
    /*
     * Clean up.
     */
    GlobalUnlock(oldData);
    GlobalUnlock(newData);
    ReleaseDC(wnd, hDC);
    SetCursor(oldCursor);

return newData;
} /* FlipHorizontal */
/*
 * FlipVertical
 *
 * This routine rotates an image about its y-axis.
 */
HANDLE FAR FlipVertical(HWND wnd, LPRECT where, HANDLE oldData) {
    char huge *oldP, huge *newP;
```

```
    int y;
HDC hDC;
    int width, height;
  long size;
HANDLE newData;
HCURSOR oldCursor;

oldCursor = SetCursor(LoadCursor(NULL, IDC_WAIT));
    /*
     * First, create a display context and select the gray palette into it.
     */
hDC = GetDC(wnd);
    SelectPalette(hDC, gPalette, 0);
    RealizePalette(hDC);
    /*
     * Now set the dimensions of the image using the rectangle.
     */
    width  = where->right - where->left;
    height = where->bottom - where->top;
    /*
     * We will need a new buffer to hold the image while we rotate it.
     */
    size = (long)width * (long)height;
newData = GlobalAlloc(GMEM_MOVEABLE, size);
if (newData == NULL) return NULL;
    /*
     * Lock both the data handles.
     */
    oldP = GlobalLock(oldData);
    newP = GlobalLock(newData);
    /*
     * Now do one row at a time, plotting the pixels as they are rotated.
     * The rotation can be accomplished by reversing each row.
     */
    newP += size-width;
    oldP += size-width;
      StartBlockDisplay(where, width);
    for (y = 0 ; y < height ; y += 1) {
        _hmemcpyb(newP+width-1, oldP, width);
        DisplayALine(hDC, newP);
        newP -= width;
        oldP -= width;
    } /* for */
    EndBlockDisplay(hDC);
    /*
     * Clean up.
     */
    GlobalUnlock(oldData);
    GlobalUnlock(newData);
    ReleaseDC(wnd, hDC);
      SetCursor(oldCursor);

return newData;
} /* FlipVertical */
/*
 * Rotate90
 *
```

```
 * This routine rotates the image 90 degrees clockwise.  The window into
 * which we are to draw has already been re-oriented.
 */
HANDLE FAR Rotate90(HWND wnd, LPRECT where, HANDLE oldData) {
    char huge *oldP, huge *o, huge *newP;
    int x, y;
    HDC hDC;
    int width, height;
    long size;
    HANDLE newData;
    HCURSOR oldCursor;

oldCursor = SetCursor(LoadCursor(NULL, IDC_WAIT));
    /*
     * First, create a display context and select the gray palette into it.
     */
    hDC = GetDC(wnd);
    SelectPalette(hDC, gPalette, 0);
    RealizePalette(hDC);
    /*
     * Now set the dimensions of the image using the rectangle.
     */
    width  = where->right - where->left;
    height = where->bottom - where->top;
    /*
     * We will need a new buffer to hold the image while we rotate it.
     */
    size = (long)width * (long)height;
    newData = GlobalAlloc(GMEM_MOVEABLE, size);
    if (newData == NULL) return NULL;
    /*
     * Lock both the data handles.
     */
    oldP = GlobalLock(oldData);
    newP = GlobalLock(newData);
    /*
     * Now do the rotation.  It can be done by copying columns from the old
     * image (starting from the right) into rows of the new image (starting
     * at the bottom).  We must keep in mind that the orientation has been
     * changed.
     */
    oldP += size;
    newP += size;
    StartBlockDisplay(where, width);
    for (y = 0 ; y < height ; y += 1) {
        o = oldP;
        for (x = 0 ; x < width ; x += 1) {
            *newP-- = *o;
            o -= height;
        } /* for */
        DisplayALine(hDC, newP+1);
        oldP--;
    } /* for */
    EndBlockDisplay(hDC);
    /*
     * Clean up.
     */
```

```
    GlobalUnlock(oldData);
    GlobalUnlock(newData);
    ReleaseDC(wnd, hDC);
    SetCursor(oldCursor);

return newData;
} /* Rotate90 */
/*
 * Rotate180
 *
 * This routine rotates an image 180 degrees, displaying it in the given
 * window inside the specified rectangle.
 */
HANDLE FAR Rotate180(HWND wnd, LPRECT where, HANDLE oldData) {
    char huge *oldP, huge *newP;
    int y;
    HDC hDC;
    int width, height;
    long size;
    HANDLE newData;
    HCURSOR oldCursor;

oldCursor = SetCursor(LoadCursor(NULL, IDC_WAIT));
    /*
     * First, create a display context and select the gray palette into it.
     */
    hDC = GetDC(wnd);
    SelectPalette(hDC, gPalette, 0);
    RealizePalette(hDC);
    /*
     * Now set the dimensions of the image using the rectangle.
     */
    width  = where->right - where->left;
    height = where->bottom - where->top;
    /*
     * We will need a new buffer to hold the image while we rotate it.
     */
    size = (long)width * (long)height;
    newData = GlobalAlloc(GMEM_MOVEABLE, size);
    if (newData == NULL) return NULL;
    /*
     * Lock both the data handles.
     */
    oldP = GlobalLock(oldData);
    newP = GlobalLock(newData);
    /*
     * Now do one row at a time, plotting the pixels as they are rotated.
     * The rotation can be accomplished by moving pixels from the beginning
     * of the old image to the end of the new, moving forward through the
     * old, and backward through the new.
     */
    newP += size-1;
    StartBlockDisplay(where, width);
    for (y = 0 ; y < height ; y += 1) {
        _hmemcpyb(newP, oldP, width);
        newP -= width;
        DisplayALine(hDC, newP+1);
        oldP += width;
```

```
    } /* for */
    EndBlockDisplay(hDC);
    /*
     * Clean up.
     */
    GlobalUnlock(oldData);
    GlobalUnlock(newData);
    ReleaseDC(wnd, hDC);
    SetCursor(oldCursor);

return newData;
} /* Rotate180 */
/*
 * Rotate270
 *
 *
 *
 */
HANDLE FAR Rotate270(HWND wnd, LPRECT where, HANDLE oldData) {
    char huge *oldP, huge *o, huge *newP;
    int x, y;
    HDC hDC;
    int width, height;
    long size;
    HANDLE newData;
    HCURSOR oldCursor;

oldCursor = SetCursor(LoadCursor(NULL, IDC_WAIT));
    /*
     * First, create a display context and select the gray palette into it.
     */
    hDC = GetDC(wnd);
    SelectPalette(hDC, gPalette, 0);
    RealizePalette(hDC);
    /*
     * Now set the dimensions of the image using the rectangle.
     */
    width  = where->right - where->left;
    height = where->bottom - where->top;
    /*
     * We will need a new buffer to hold the image while we rotate it.
     */
    size = (long)width * (long)height;
    newData = GlobalAlloc(GMEM_MOVEABLE, size);
    if (newData == NULL) return NULL;
    /*
     * Lock both the data handles.
     */
    oldP = GlobalLock(oldData);
    newP = GlobalLock(newData);
    /*
     * Now do the rotation.  It can be done by copying columns from the old
     * image (starting from the right) into rows of the new image (starting
     * at the bottom).  We must keep in mind that the orientation has been
     * changed.
     */
    newP += size;
    StartBlockDisplay(where, width);
```

```
    for (y = 0 ; y < height ; y += 1) {
       o = oldP;
       for (x = 0 ; x < width ; x += 1) {
          *newP-- = *o;
          o -= height;
       } /* for */
       DisplayALine(hDC, newP+1);
       oldP++;
    } /* for */
    EndBlockDisplay(hDC);
    /*
     * Clean up.
     */
    GlobalUnlock(oldData);
    GlobalUnlock(newData);
    ReleaseDC(wnd, hDC);
    SetCursor(oldCursor);

return newData;
} /* Rotate270 */

WINDOW_PROC TemplateWindow(HWND, WORD, WORD, LONG);

#include "windows.h"
#include "btrieve.h"
#include "wdpx.h"
#include "resource.h"
#include "wdpxdlg.h"
#pragma hdrstop
#include "tmplwnd.h"
#include "messages.h"
#include "wndwords.h"
/*
 * StartAcquireEnum
 *
 * Local routine called by EnumChildWindows when an acquisition is started.
 * It needs to clear the flags of all the children so that they show up
 * as empty.
 */
static BOOL FAR PASCAL _export StartAcquireEnum(HWND wnd, DWORD lP) {
    SetWindowWord(wnd, TCHILD_W_Data, 0);

return TRUE;
} /* StartAcquireEnum */
/*
 * ColorChangeEnum
 *
 * Local routine called by EnumChildWindows when a color change occurs.  The
 * lP field is not used.
 */
static BOOL FAR PASCAL _export ColorChangeEnum(HWND wnd, DWORD lP) {
    SendMessage(wnd, WM_SYSCOLORCHANGE, 0 ,0);

return TRUE;
} /* ColorChangeEnum */
/*
 * ModeChangeEnum
 *
```

```c
 * Local routine called by EnumChildWindows when a mode change occurs.  The
 * IP field is used to hold the new mode.
 */
static BOOL FAR PASCAL _export ModeChangeEnum(HWND wnd, DWORD IP) {
    SendMessage(wnd, DPX_ChangeMode, IP ,0);

return TRUE;
} /* ModeChangeEnum */
/*
 * CreateTemplate
 *
 * Local routine to fill the template.
 */
static void CreateTemplate(HWND wnd) {
    StudiesPtr study;
    int wheight, wwidth;
    long top, left, height, width;
    int twidth, theight;
    int images;
    ExamTypes exam_type;
    Orientations o;
    int ellipse;
    int i;
    RECT rect;
    HWND child;
    /*
     * Get the size of the window.
     */
    GetClientRect(wnd, &rect);
    wwidth = rect.right;
    wheight = rect.bottom;

study = (StudiesPtr)GlobalLock(ghStudy);
    /*
     * Get the information to compute the scaling factor for this template.
     */
    exam_type = study->exam_type;

twidth  = intra_modes[exam_type].mmWidth;
    theight = intra_modes[exam_type].mmHeight;

images = intra_modes[exam_type].numImages;
    /*
     * Now use these values to create the sub-windows for the template.
     */
    width   = 40L * wwidth  / twidth;
    height  = 30L * wheight / theight;
    ellipse =  5L * wwidth  / twidth;
    for (i = 0 ; i < images ; i += 1) {
        int w,h;
    left = intra_modes[exam_type].images[i].corner.x;
    top  = intra_modes[exam_type].images[i].corner.y;
    o    = intra_modes[exam_type].images[i].portrait;

left = left * wwidth  / twidth;
    top  = top  * wheight / theight;
```

```
            w = (o == landscape) ? width : height;
            h = (o == landscape) ? height : width;
             child = CreateWindow("templateChildWClass",
                        NULL,
                        WS_CHILDWINDOW|WS_VISIBLE,
                         left,
                         top,
                         w,
                         h,
                         wnd,
                         i,
                         GetWindowWord(wnd, GWW_HINSTANCE),
                        NULL
                         );
            if (!child) {
                MessageBox(wnd, "Cannot create template",
                        NULL,
                        MB_OK|MB_SYSTEMMODAL|MB_ICONSTOP);
            } /* if */
            SetWindowWord(child, TCHILD_W_Data, i == 0);
        } /* for */
        /*
         * Define the ellipse value and mode for the children.
         */
        child = GetWindow(wnd, GW_CHILD);
         SetClassWord(child, TCHILD_C_Ellipse, ellipse);
        /*
         * Cleanup.
         */
        GlobalUnlock(ghStudy);
} /* CreateTemplate */
/*
 * DestroyTemplate
 *
 * Local routine to clean up the child windows.
 */
static void DestroyTemplate(HWND wnd) {
    HWND child;

while ((child = GetWindow(wnd, GW_CHILD)) != NULL) {
        DestroyWindow(child);
    } /* while */
} /* DestroyTemplate */
/*
 * SizeTemplate
 *
 * Local routine to re-size the template to fit in the space.
 */
static void SizeTemplate(HWND wnd, StudiesPtr s) {
    double screen, physical;
     int wwidth, wheight, wX, wY;
     int twidth, theight;
    ExamTypes exam_type;
     int width, height;
    int X, Y;

exam_type = s->exam_type;
```

```
     wX      = GetWindowWord(wnd, TMPL_W_FreeLeft);
     wY      = GetWindowWord(wnd, TMPL_W_FreeTop);
     wwidth  = GetWindowWord(wnd, TMPL_W_FreeWidth);
     wheight = GetWindowWord(wnd, TMPL_W_FreeHeight);
     screen  = (double)wwidth / (double)wheight;

twidth   = intra_modes[exam_type].mmWidth;
     theight  = intra_modes[exam_type].mmHeight;
     physical = (double)twidth / (double)theight;

if (physical <= screen) {
        height = wheight;
        width  = wheight * physical;
     } else {
        width  = wwidth;
        height = width / physical;
     } /* if */

X = wX + (wwidth - width)/2;
     Y = wY + (wheight - height)/2;
     MoveWindow(wnd, X, Y, width, height, FALSE);
} /* SizeTemplate */
/*
 * TemplateWindow
 *
 * This is the main callback routine for the window which is used to display
 * a template for retrieving intraoral images.
 */
WINDOW_PROC TemplateWindow(HWND wnd, WORD msg, WORD wP, LONG lP) {
     LONG retVal = NULL;
     StudiesPtr study;
     FARPROC enumProc;
     RECT rect;
     HWND cWnd;

switch (msg) {
     case WM_SYSCOLORCHANGE:
        /*
         * Create a new brush the same color as the background, and invalidate
         * all the children who are affected.
         */
        DeleteObject(ghChildBrush);
        ghChildBrush = CreateSolidBrush(GetSysColor(COLOR_BACKGROUND));

enumProc = MakeProcInstance((FARPROC)ColorChangeEnum, gInst);
        EnumChildWindows(wnd, enumProc, 0);
        FreeProcInstance(enumProc);
        break;
     case DPX_StartAcquire:
        enumProc = MakeProcInstance((FARPROC)StartAcquireEnum, gInst);
        EnumChildWindows(wnd, enumProc, 0);
        FreeProcInstance(enumProc);
        break;
     case DPX_ChangeStudy:
        if (!gAcquiring) {
           /*
            * Here, if the current study is an intraoral, display the appropriate
```

```
       * template.
       */
        study = (StudiesPtr)GlobalLock(ghStudy);
        if (study->modality == intra_mode) {
         ShowWindow(wnd, SW_HIDE);
          DestroyTemplate(wnd);
          SizeTemplate(wnd, study);
          CreateTemplate(wnd);
         ShowWindow(wnd, SW_SHOW);
          SetWindowWord(wnd, TMPL_W_ImageNumber, 0);
          /*
           * Keep the image handle.
           */
          SetClassWord(GetWindow(wnd, GW_CHILD), TCHILD_C_ImageHandle,
wP);
          SetClassWord(GetWindow(wnd, GW_CHILD), TCHILD_C_Message, msg);
        } else {
          ShowWindow(wnd, SW_HIDE);
           DestroyTemplate(wnd);
         } /* if */
         GlobalUnlock(ghStudy);
       } /* if */
     break;
   case DPX_EndAcquire:
       /*
        * If wP is TRUE, then the acquisition was completed normally.  The
        * window need to remain, but changing over into study review mode.
        * Otherwise,we can just fall through into the close-up case.
        */
       if (wP) {
         break;
       } /* if */
   case DPX_ImagePlaced:
       /*
        * When we get an image stored message, we need to update the child.
        */
       cWnd = GetDlgItem(wnd, wP);
       SetWindowWord(cWnd, TCHILD_W_Data, 1);
        GetClientRect(cWnd, &rect);
        InvalidateRect(cWnd, &rect, FALSE);
     break;
    case DPX_ClearPatient:
    case DPX_ChangePatient:
       /*
        * In any of these cases, we should hide the window and destroy and
        * the child windows.
        */
       ShowWindow(wnd, SW_HIDE);
        DestroyTemplate(wnd);
      break;
    case DPX_ChangeImage:
       /*
        * Tell the image window and the two children involved that the image
        * has changed.
        */
        PostMessage(GetDlgItem(wnd, GetWindowWord(wnd, TMPL_W_ImageNumber)),
            DPX_ChangeImage,
```

```
                    FALSE,
                    0);
            PostMessage(GetDlgItem(wnd, wP),
                    DPX_ChangeImage,
                    TRUE,
                    0);
            PostMessage(gImageWnd,
                    DPX_ChangeImage,
                    wP,
                    0);
            SetWindowWord(wnd, TMPL_W_ImageNumber, wP);
            break;
        case DPX_ChangeMode:
            /*
             * Hide or show the window based upon the value of wP.  If changing
             * to automatic mode, tell each child so that they can get rid of the
             * manual image window associated.  If switching to manual mode,
             * we need only tell the selected child.
             *     wP = TRUE => switching to automatic mode.
             */
            if (wP) {
                enumProc = MakeProcInstance((FARPROC)ModeChangeEnum, gInst);
                EnumChildWindows(wnd, enumProc, wP);
                FreeProcInstance(enumProc);
                ShowWindow(gImageWnd, SW_SHOW);
            } else {
                PostMessage(GetDlgItem(wnd, GetWindowWord(wnd,
TMPL_W_ImageNumber)),
                        DPX_ChangeMode,
                        FALSE,
                        0);
                ShowWindow(gImageWnd, SW_HIDE);
            } /* if */
            break;
        default:
            retVal = DefWindowProc(wnd, msg, wP, lP);
            break;
    } /* switch */ return retVal;
} /* TemplateWindow */

WINDOW_PROC TemplateChildWindow(HWND, WORD, WORD, LONG);

#include "windows.h"
#include "btrieve.h"
#include "wdpx.h"
#include "resource.h"
#include "wdpxdlg.h"
#pragma hdrstop
#include "tmplchld.h"
#include "messages.h"
#include "manwnd.h"
#include "study.h"
#include "wndwords.h"
/*
 * Local variables used when dragging the outline of a window which will be
 * used to display the image when the user releases the mouse.
```

```
*/
static RECT dragRect;              /* Rectangle most recently drawn. */
static POINT dragPoint;            /* Location of last mouse move message. */
/*
 * TemplateChildWindow
 *
 * This is the main callback routine for the window which is used to display
 * a template for retrieving intraoral images.
 */
WINDOW_PROC TemplateChildWindow(HWND wnd, WORD msg, WORD wP, LONG lP) {
  LONG retVal = NULL;
  HDC hDC;
  PAINTSTRUCT ps;
  RECT rect;
  BOOL removed;
  HANDLE oldBrush;
   int ellipse;
  HWND imageWnd;
   StudiesPtr s;
   int selWindow;
  BOOL manualMode;

switch (msg) {
  case DPX_ChangeMode:
     /*
      * Handle the worked associated with changing modes.  If switching to
      * automatic mode (wP = TRUE), destroy the sub-window (if there is
      * one).  Then determine if this window is to be removed.  When
      * switching to manual mode, just clear the removed field.
      */
     GetClientRect(wnd, &rect);
     if (wP) {
        imageWnd = GetWindowWord(wnd, TCHILD_W_Data);
        if (imageWnd) {
           DestroyWindow(imageWnd);
           SetWindowWord(wnd, TCHILD_W_Data, 0);
           InvalidateRect(wnd, &rect, FALSE);
        } /* if */ selWindow = GetWindowWord(GetParent(wnd), TMPL_W_ImageNumber);
        if (selWindow == GetWindowWord(wnd, GWW_ID)) {
           SetWindowWord(wnd, TCHILD_W_Data, TRUE);
           InvalidateRect(wnd, &rect, FALSE);
        } /* if */
     } else {
        SetWindowWord(wnd, TCHILD_W_Data, FALSE);
        InvalidateRect(wnd, &rect, FALSE);
     } /* if */
     break;
  case DPX_ChangeImage:
       SetWindowWord(wnd, TCHILD_W_Data, wP);
       GetClientRect(wnd, &rect);
       InvalidateRect(wnd, &rect, FALSE);
     break;
  case WM_DESTROY:
     /*
      * On a destroy message, if in manual mode, the sub-image should
      * be removed.
```

```
         */
         imageWnd = GetWindowWord(wnd, TCHILD_W_Data);
         if (IsWindow(imageWnd)) {
            DestroyWindow(imageWnd);
         } /* if */
      break;
   case WM_SYSCOLORCHANGE:
      /*
       * On a color change, all child windows which have a non-zero value
       * in word 0 should be re-drawn, to take into account a possible
       * change in background color.
       */
      if (GetWindowWord(wnd, TCHILD_W_Data)) {
         GetClientRect(wnd, &rect);
         InvalidateRect(wnd, &rect, FALSE);
      } /* if */
   case WM_PAINT:
      manualMode = SendDlgItemMessage(gPatDlg, IDC_PTD_MANUAL,
                     BM_GETCHECK,
                        0,
                        0);
      if (gAcquiring) {
         removed = !GetWindowWord(wnd, TCHILD_W_Data);
      } if (manualMode) {
         imageWnd = GetWindowWord(wnd, TCHILD_W_Data);
         removed  = imageWnd != 0 && IsWindowVisible(imageWnd);
      } else {
         removed = GetWindowWord(wnd, TCHILD_W_Data);
      } /* if */
      ellipse = GetClassWord(wnd, TCHILD_C_Ellipse);
      /*
       * Get a device context.
       */
      hDC = BeginPaint(wnd, &ps);
      /*
       * Get the correct brush with which to fill the rectangle.
       */
      if (removed)
         oldBrush = SelectObject(hDC, ghChildBrush);
      else
         oldBrush = SelectObject(hDC, GetStockObject(DKGRAY_BRUSH));
      /*
       * Fill the window (or a rounded rectangle version of it).
       */
      GetClientRect(wnd, &rect);
      RoundRect(hDC, 0,
            0,
               rect.right,
               rect.bottom,
               ellipse,
               ellipse);
      /*
       * Clean up.
       */
      SelectObject(hDC, oldBrush);
      EndPaint(wnd, &ps);
      break;
```

```
case WM_LBUTTONDOWN:
    /*
     * Check to see if the program is in automatic or manual mode.
     */
    manualMode = SendDlgItemMessage(gPatDlg, IDC_PTD_MANUAL,
                    BM_GETCHECK,
                    0,
                    0);
    if (manualMode) {
        /*
         * Manual mode.  If this image is already in a window, bring it
         * to the front.  Otherwise, capture the mouse and begin dragging
         * an outline around.
         */
        imageWnd = GetWindowWord(wnd, TCHILD_W_Data);
        if (imageWnd) {
            if (IsWindowVisible(imageWnd)) {
                SetFocus(imageWnd);
            } else {
                ShowWindow(imageWnd, SW_SHOW);
                GetClientRect(wnd, &rect);
                InvalidateRect(wnd, &rect, FALSE);
            } /* if */
        } else {
            int width, height;
            s = (StudiesPtr)GlobalLock(ghStudy);
            SetCapture(wnd);
            /*
             * Define the rectangle taking the image orientation into
             * account.
             */
            dragPoint.x = LOWORD(lP);
            dragPoint.y = HIWORD(lP);
            ClientToScreen(wnd, &dragPoint);
            dragRect.left  = dragPoint.x;
            dragRect.top   = dragPoint.y;
            GetStudyDimensions(s, GetWindowWord(wnd, GWW_ID), &width,
                                        &height);
            dragRect.right = dragRect.left +
                    width +
                    2*GetSystemMetrics(SM_CXFRAME) +
                    1;
            dragRect.bottom = dragRect.top +
                    height +
                    2*GetSystemMetrics(SM_CYFRAME) +
                    GetSystemMetrics(SM_CYCAPTION) +
                    1;
            /*
             * Now get a device context, and draw the first rectangle.
             */
            hDC = CreateDC("DISPLAY", NULL, NULL, NULL);
            SetROP2(hDC, R2_XORPEN);
            SelectObject(hDC, GetStockObject(WHITE_PEN));
            SelectObject(hDC, GetStockObject(NULL_BRUSH));
            Rectangle(hDC, dragRect.left,
                    dragRect.top,
                    dragRect.right,
```

```
                        dragRect.bottom);
            DeleteDC(hDC);

GlobalUnlock(ghStudy);
         } /* if */
      } else {
        /*
         * Automatic mode.  If this image is not already removed, send
         * a message to the template indicating the change.
         */
         if (!GetWindowWord(wnd, TCHILD_W_Data)) {
            PostMessage(gTemplateWnd, DPX_ChangeImage,
                         GetWindowWord(wnd, GWW_ID),
                         0);
         } /* if */
      } /* if */
      break;
   case WM_MOUSEMOVE:
      if (GetCapture() == wnd) {
        /*
         * Now get a device context, undraw the old rectangle and draw
         * the new rectangle.
         */
         hDC = CreateDC("DISPLAY", NULL, NULL, NULL);
         SetROP2(hDC, R2_XORPEN);
            SelectObject(hDC, GetStockObject(WHITE_PEN));
            SelectObject(hDC, GetStockObject(NULL_BRUSH));
            Rectangle(hDC, dragRect.left,
                     dragRect.top,
                     dragRect.right,
                     dragRect.bottom);

dragPoint.x = LOWORD(lP);
         dragPoint.y = HIWORD(lP);
            ClientToScreen(wnd, &dragPoint);
            dragRect.right  += (dragPoint.x-dragRect.left);
            dragRect.bottom += (dragPoint.y-dragRect.top);
         dragRect.left = dragPoint.x;
          dragRect.top  = dragPoint.y;
            Rectangle(hDC, dragRect.left,
                     dragRect.top,
                     dragRect.right,
                     dragRect.bottom);
         DeleteDC(hDC);
      } else {
         retVal = DefWindowProc(wnd, msg, wP, lP);
      } /* if */
      break;
   case WM_LBUTTONUP:
      if (GetCapture() == wnd) {
        /*
         * First undraw the rectangle.
         */
         hDC = CreateDC("DISPLAY", NULL, NULL, NULL);
         SetROP2(hDC, R2_XORPEN);
            SelectObject(hDC, GetStockObject(WHITE_PEN));
            SelectObject(hDC, GetStockObject(NULL_BRUSH));
```

```
                    Rectangle(hDC, dragRect.left,
                            dragRect.top,
                                dragRect.right,
                                dragRect.bottom);
            DeleteDC(hDC);

ReleaseCapture();
            /*
             * Now create the new window for the image.  I'm not entirely
             * sure why, but we need to subtract one extra from the vertical
             * dimension.  Probably has something to do with the combined
             * size of the caption and the frame.
             */
            imageWnd = CreateWindow("manualWClass",
                            NULL,
                            WS_CAPTION | WS_THICKFRAME |
                                WS_POPUP |
                                WS_MINIMIZEBOX |
                                WS_MAXIMIZEBOX |
                                WS_VSCROLL |
                                WS_HSCROLL,
                            dragRect.left,
                            dragRect.top,
                                dragRect.right-dragRect.left-1,
                                dragRect.bottom-dragRect.top-1,
                            wnd,
                            NULL,
                                gInst,
                            NULL
                            );
            SetWindowWord(imageWnd, MAN_W_ImageNumber, GetWindowWord(wnd,
GWW_ID));
            SetClassWord(imageWnd, MAN_C_ImageHandle, GetClassWord(wnd,
TCHILD_C_ImageHandle));
            SetWindowWord(wnd, TCHILD_W_Data, imageWnd);
            GetClientRect(wnd, &rect);
            InvalidateRect(wnd, &rect, FALSE);
            ShowWindow(imageWnd, SW_SHOW);
        } else {
            retVal = DefWindowProc(wnd, msg, wP, lP);
        } /* if */
        break;
    default:
        retVal = DefWindowProc(wnd, msg, wP, lP);
        break;
    } /* switch */ return retVal;
} /* TemplateChildWindow */ void SetAcquireDim(Modalities modality, int x, int y, BOOL rewrite);
void GetAcquireDim(Modalities modality, short *x, short *y);
BOOL AcquireStudy(HANDLE buffer);
void AcquisitionToolPalette(void);
```

```c
#include "windows.h"
#include "btrieve.h"
#include "wdpx.h"
#include "resource.h"
#include "wdpxdlg.h"
#pragma hdrstop
#include "acquire.h"
#include "acqcntl.h"
#include "study.h"
#include "studydb.h"
#include "toolwnd.h"
#include "utils.h"
#include "wndwords.h"

include <io.h> static char textBuffer[128];
static long intra_x;
static long intra_y;
static long pano_x;
static long pano_y;
/*
 * SetAcquireDim
 *
 * This routine is called whenever the user changes the size of acquired
 * images.
 */
void SetAcquireDim(Modalities modality, int x, int y, BOOL rewrite) {
    switch (modality) {
    case pano_mode:
        pano_x = x;
        pano_y = y;
        break;
    case intra_mode:
        intra_x = x;
        intra_y = y;
        break;
    } /* switch */
    if (rewrite) {
        wsprintf(textBuffer, "%ld,%ld,%ld,%ld", pano_x, pano_y,
                                        intra_x, intra_y);
        WriteProfileString(gAppName, "Acquire sizes", textBuffer);
    } /* if */
} /* SetAcquireDim */
/*
 * GetAcquireDim
 *
 * This routine returns the acquire sizes for a study of the indicated size.
 */
void GetAcquireDim(Modalities modality, short *x, short *y) {
    switch (modality) {
    case pano_mode:
        *x = pano_x;
        *y = pano_y;
        break;
    case intra_mode:
        *x = intra_x;
```

```
        *y = intra_y;
        break;
    } /* switch */
} /* GetAcquireDim */
/*
 * AcquirePano
 *
 * Local routine to control the acquisition of a panoramic X-Ray.
 */
static BOOL AcquirePano(HANDLE buffer) {
    return TRUE;
} /* AcquirePano */
/*
 * AcquireIntra
 *
 * Local routine to control the acquisition of a series of intraoral x-rays.
 */
static BOOL AcquireIntra(HANDLE buffer) {
    return TRUE;
} /* AcquireIntra */
/*
 * AcquireStudy
 *
 * This routine controls the acquisition of any type of study.
 * Naturally, it makes heavy use of the more specific local routines in
 * this source file.  It acquires based upon the study stored in the global
 * study record.
 */
BOOL AcquireStudy(HANDLE buffer) {
  BOOL retVal = TRUE;
    StudiesPtr s = (StudiesPtr)GlobalLock(ghStudy);
    Modalities mode = (Modalities)s->modality;

GlobalUnlock(ghStudy);
    switch (mode) {
    case pano_mode:
        retVal = AcquirePano(buffer);
      break;
    case intra_mode:
        retVal = AcquireIntra(buffer);
      break;
    default:
        wsprintf(textBuffer, "I do not know how to acquire %s images",
mode_strings[s->modality]);
      MessageBox(GetFocus(),
            textBuffer,
            "Acquire Problem",
        MB_OK|MB_ICONINFORMATION|MB_APPLMODAL);
      retVal = FALSE;
      break;
    } /* switch */ return retVal;
} /* AcquireStudy */
/*
 * AcquisitionToolPalette
 *
```

```
 * This routine adds the acquisition tools to the tool window and displays
 * the window.
 */
void AcquisitionToolPalette(void) {
  HICON theIcon;
  /*
   * If the tool window is visible, hide it.
   */
   if (IsWindowVisible(gToolWnd))
     ShowWindow(gToolWnd, SW_HIDE);
  /*
   * Remove all tools from the window.
   */
   SendMessage(gToolWnd, TM_ClearTools, 0, 0);
  /*
   * Now lead each icon and add the tools.
   * First the flip horizontal tool.
   */
   theIcon = LoadIcon(gInst, "Flip_Around_Horz");
   SendMessage(gToolWnd, TM_AddTool, theIcon, 0);
  /*
   * Now the flip vertical tool.
   */
   theIcon = LoadIcon(gInst, "Flip_Around_Vert");
   SendMessage(gToolWnd, TM_AddTool, theIcon, 0);
  /*
   * Now the rotate -90 tool.
   */
   theIcon = LoadIcon(gInst, "Rotate_270");
   SendMessage(gToolWnd, TM_AddTool, theIcon, 0);
  /*
   * Now the rotate 90 tool.
   */
   theIcon = LoadIcon(gInst, "Rotate_90");
   SendMessage(gToolWnd, TM_AddTool, theIcon, 0);
  /*
   * Now the rotate 180 tool.
   */
   theIcon = LoadIcon(gInst, "Rotate_180");
   SendMessage(gToolWnd, TM_AddTool, theIcon, 0);
  /*
   * Now the auto drop tool.
   */
   theIcon = LoadIcon(gInst, "Hand");
   SendMessage(gToolWnd, TM_AddTool, theIcon, (long)DoDropTool);
  /*
   * Show the window.
   */
   ShowWindow(gToolWnd, SW_SHOW);
} /* AcquisitionToolPalette */
```

What is claimed is:

1. A method of displaying stored intra-oral radiographs, comprising:
   displaying a representation of an intra-oral radiograph holder including target intra-oral radiological sites arranged according to anatomical location of said sites;
   selecting one of said target intra-oral radiological sites; and
   displaying a stored intra-oral radiograph corresponding to said selected target intra-oral radiological site.

2. A method for storing and displaying intra-oral radiographs, comprising:
   generating and displaying intra-oral radiographs of dentition;
   generating and displaying a representation of an intra-oral radiograph holder including selectable intra-oral radiological sites arranged according to anatomical location of said sites;
   storing said intra-oral radiograph images responsive to selection of intra-oral radiological sites in said representation along with indicia of respective selected intra-oral radiological sites; and
   subsequently retrieving and displaying said intra-oral radiographs responsive to selection of respective intra-oral radiological sites in said representation.

3. A program storage device readable by a machine and tangibly embodying a representation of a program of instructions adaptable to be executed by said machine to perform the method of any one of claims 1 or 2.

4. A device for storing and displaying intra-oral radiographs, comprising:
   an x-ray source;
   a sensor for producing x-ray images of dentition placed between said source and said sensor;
   a memory in which said x-ray images are stored;
   a display;
   means for generating and displaying on said display a representation of an intra-oral radiograph holder including selectable intra-oral radiological sites arranged according to anatomical location of said sites; and
   means, responsive to selection of said selectable sites, for displaying corresponding stored x-ray images.

5. The device of claim 4, further comprising:
   an image digitizer for digitizing x-ray images produced by said sensor before storage in said memory.

* * * * *